US009618516B2

(12) United States Patent
Treiber et al.

(10) Patent No.: US 9,618,516 B2
(45) Date of Patent: Apr. 11, 2017

(54) HOMOGENOUS THERMAL SHIFT LIGAND BINDING ASSAY

(71) Applicant: DiscoveRx Corporation, Fremont, CA (US)

(72) Inventors: Daniel K. Treiber, San Diego, CA (US); Elena Menichelli, San Diego, CA (US)

(73) Assignee: DISCOVERX CORPORATION, Fremont, CA (US)

( * ) Notice: Subject to any disclaimer, the term of this patent is extended or adjusted under 35 U.S.C. 154(b) by 0 days.

(21) Appl. No.: 14/830,328

(22) Filed: Aug. 19, 2015

(65) Prior Publication Data

US 2016/0054322 A1    Feb. 25, 2016

Related U.S. Application Data

(60) Provisional application No. 62/087,671, filed on Dec. 4, 2014, provisional application No. 62/040,294, filed on Aug. 21, 2014.

(51) Int. Cl.
    *G01N 33/573*    (2006.01)
    *G01N 33/58*     (2006.01)
    *G01N 33/542*    (2006.01)

(52) U.S. Cl.
    CPC ......... *G01N 33/581* (2013.01); *G01N 33/542* (2013.01); *G01N 2333/938* (2013.01); *G01N 2500/04* (2013.01)

(58) Field of Classification Search
    CPC .................................................. G01N 2500/04
    See application file for complete search history.

(56) References Cited

U.S. PATENT DOCUMENTS

| | | | |
|---|---|---|---|
| 4,708,929 | A | 11/1987 | Henderson |
| 6,020,141 | A | 2/2000 | Pantoliano et al. |
| 6,036,920 | A | 3/2000 | Pantoliano et al. |
| 6,291,191 | B1 | 9/2001 | Pantoliano et al. |
| 6,828,099 | B2 | 12/2004 | Michnick et al. |
| 7,235,374 | B2 * | 6/2007 | Palmer ................. G01N 33/566 435/69.7 |
| 8,586,294 | B2 | 11/2013 | Blau et al. |
| 8,945,853 | B2 | 2/2015 | Raab et al. |
| 2002/0068298 | A1 | 6/2002 | Tomich et al. |
| 2004/0137480 | A1 | 7/2004 | Eglen |
| 2007/0105093 | A1 | 5/2007 | Ciceri et al. |
| 2008/0058219 | A1 | 3/2008 | Lockhart et al. |
| 2008/0176248 | A1 | 7/2008 | Lockhart et al. |
| 2009/0053701 | A1 | 2/2009 | Ciceri et al. |
| 2010/0203555 | A1 | 8/2010 | Wehrman et al. |
| 2014/0045194 | A1 | 2/2014 | Wehrman et al. |
| 2014/0057368 | A1 | 2/2014 | Nordlund |

FOREIGN PATENT DOCUMENTS

| | | |
|---|---|---|
| WO | 96/30540 A2 | 10/1996 |
| WO | 2010037718 A1 | 4/2010 |
| WO | 2012/143714 A1 | 10/2012 |
| WO | 2013/119579 A1 | 8/2013 |

OTHER PUBLICATIONS

Bessman, M.J., et al., "The MutT Proteins or 'Nudix' Hydrolases, a Family of Versatile, Widely Distributed, 'Housecleaning' Enzymes," The Journal of Biological Chemistry (1996) 271(41)25059-25062.
Eglen, R.M., "Enzyme Fragment Complementation: A Flexible High Throughput Screening Assay Technology," Assay and Drug Development Technologies (2002) vol. 1, No. 1-1, 97-104.
Eglen, R.M. and Singh, R., "β Galactosidase Enzyme Fragment Complementation as a Novel Technology for High Throughput Screening," Combinatorial Chemistry & High Throughput Screening (2003) 6:381.387.
Filippakopoulos P., et al., "Selective inhibition of BET bromodomains," Nature (2010) 468(7327):1067-1073.
Galarneau, A., et al., "β-Laclamase protein fragment complementation assays in vivo and in vitro sensors of protein-protein interactions," Nature Biotech. (2002) 20:619-622.
Jung, M., et al., "Affinity Map of Bromodomain Protein 4 (BRD4) Interactions with the Histone H4 Tail and the Small Molecule Inhibitor JQ1," J. Biol. Chem. (2014) 289:9304-9319.
Layton, C.J. and Hellinga, H.W., "Quantitation of protein-protein interactions by thermal stability shift analysis," Protein Science (2011) 20:1439-1450.
Mohler, W.A. and Blau, H.M, "Gene expression and cell fusion analyzed by lacz complementation in mammalian cells," Proc. Natl. Acad. Sci. USA (1996) 93:12423-12427.
Molina, D.M., et al., "Monitoring Drug Target Engagement in Cells and Tissues Using the Cellular Thermal Shift Assay," Science (2013) 341:84-87.
Nolan, G.P., et al., "Fluorescence-activated cell analysis and sorting of viable mammalian cells based on β-D-galactosidase activity after transduction of *Escherichia coli* lacZ," Proc. Natl. Acad. Sci. USA (1988) 85:2603-2607.

(Continued)

*Primary Examiner* — Bin Shen
(74) *Attorney, Agent, or Firm* — Brian E. Davy; Bozicevic, Field & Francis LLP

(57) ABSTRACT

Disclosed are methods for detecting and quantitatively measuring a binding property of a compound to a target macromolecule, wherein the target macromolecule is subject to denaturation and is linked to a labeling peptide, such as a short enzyme fragment. The method uses a fluid mixture comprising (i) a chimeric molecule comprising a target macromolecule linked to the labeling peptide and (ii) a compound being measured for binding to the target macromolecule, wherein said target macromolecule is subject to denaturation. After allowing for binding of the compound (e.g. a small molecule inhibitor of the target macromolecule), one detects a signal from the labeling peptide, such as by enzyme fragment complementation. This signal indicates a differential between denatured and non-denatured target macromolecules and thereby indicates a differential between target macromolecules not bound to the compound and target macromolecules bound to the compound, respectively.

22 Claims, 13 Drawing Sheets

(56) References Cited

OTHER PUBLICATIONS

Remy, I. and Michnick, S.W., "Clonal selection and in vivo quantitation at protein interactions with protein-fragment complementation assays," Proc. Natl. Acad. Sci. USA (1999) 96:5394-5399.

Rotman, B., et al., "Fluorogenic Substrates for β-D-Galactosidases and Phosphatases Derived from Fluorescein (3,6-Dihydroxyfluoran) and its Monomethyl Ether," Proc. Natl. Acad. Sci. USA (1963) 50:1-6.

Spotts, J.M., et al., "Time-lapse imaging of a dynamic phosphorylation-dependent protein-protein interaction in mammalian cells," Proc. Natl. Acad. Sci. USA (2002) 99(23):15142-15147.

Strickland, E.C., et al., "Thermodynamic Analysis of Protein-Ligand Binding Interactions in Complex Biological Mixtures using the Stability of Proteins from Rates of Oxidation (SPROX) Method," Nat Protoc. (2013) 8(1):148-161.

Wehrman, T.S., et al., "Enzymatic detection of protein translocation," Nature Methods (2005) 2(7):521-527.

International Search Report and Written Opinion, Int'l. Appl. No. PCT/US2015/045736, Nov. 23, 2015.

* cited by examiner

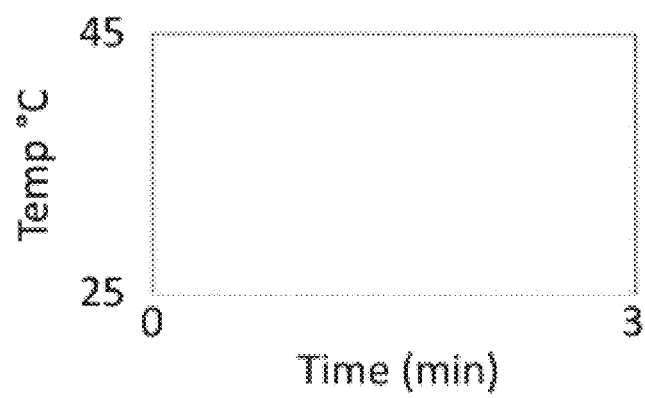
8A: Standard Denaturation Profile
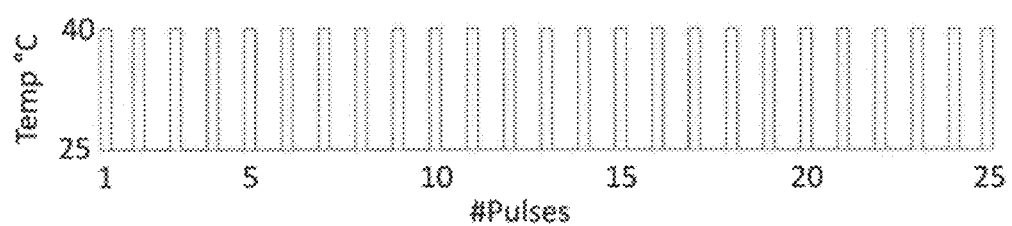
8B: Pulse Denaturation Profile

SEQUENCE LISTING

<160> NUMBER OF SEQ ID NOS: 4

<210> SEQ ID NO 1
<211> LENGTH: 52
<212> TYPE: PRT
<213> ORGANISM: E. coli
<220> FEATURE:
<221> NAME/KEY: PEPTIDE
<222> LOCATION: (1)..(52)

```
<223> OTHER INFORMATION: Wild-type ED

<400> SEQUENCE: 1

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Glu Glu Ala Arg Thr Asp Arg Pro
            35                  40                  45

Ser Gln Gln Leu
    50

<210> SEQ ID NO 2
<211> LENGTH: 42
<212> TYPE: PRT
<213> ORGANISM: E. coli
<220> FEATURE:
<221> NAME/KEY: PEPTIDE
<222> LOCATION: (1)..(42)
<223> OTHER INFORMATION: Prolabel ED

<400> SEQUENCE: 2

Asn Ser Leu Ala Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
                20                  25                  30

Arg Asn Ser Glu Glu Ala Arg Thr Asp Arg
            35                  40

<210> SEQ ID NO 3
<211> LENGTH: 52
<212> TYPE: PRT
<213> ORGANISM: E. coli
<220> FEATURE:
<221> NAME/KEY: PEPTIDE
<222> LOCATION: (1)..(52)
<223> OTHER INFORMATION: W34Y ED

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Tyr Arg Asn Ser Glu Glu Ala Arg Thr Asp Arg Pro
            35                  40                  45

Ser Gln Gln Leu
    50

<210> SEQ ID NO 4
<211> LENGTH: 42
<212> TYPE: PRT
<213> ORGANISM: E. coli
<220> FEATURE:
<221> NAME/KEY: PEPTIDE
<222> LOCATION: (1)..(42)
<223> OTHER INFORMATION: Enhanced Prolabel ED

<400> SEQUENCE: 4
```

-continued

```
Asn Ser Leu Ala Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
                20                  25                  30

Arg Asn Ser Glu Glu Ala Arg Thr Asp Arg
            35                  40
```

HOMOGENOUS THERMAL SHIFT LIGAND BINDING ASSAY

CROSS-REFERENCE TO RELATED APPLICATIONS

This application claims priority from U.S. Provisional Patent Application No. 62/087,671, filed Dec. 4, 2014, and U.S. Provisional Patent Application No. 62/040,294, filed Aug. 21, 2014, both of which are hereby incorporated by reference in their entirety.

STATEMENT OF GOVERNMENTAL SUPPORT

None.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on Aug. 18, 2015, is named "3817_54_1_seq_list.txt" and is 2,524 bytes in size.

BACKGROUND OF THE INVENTION

Field of the Invention

The present invention relates generally to methods of monitoring binding of a compound to a target macromolecule by increasing the thermal stability of the target macromolecule. The present invention also relates to a novel method of use of enzyme fragment complementation.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

A number of areas of biology and medicine depend on and develop assays to detect ligand binding to proteins and/or protein fragments. The binding assays help in determining a target which should be safe and druggable. The multibillion dollar pharmaceutical industry depends on these assays to find a drug compound that has an ability to bind to its target protein to perform its function.

A number of protein-ligand interaction assays have been developed and discussed in the past such as labeled and label-free ligand binding assays, structure-based ligand binding assays, thermodynamic ligand binding assays and whole cell ligand binding assays. Further, there is a fluorescence based ligand binding assay wherein a fluorescently labeled ligand binds to a target macromolecule. However, the assay is susceptible to different fluorescence interference and thus leads to undesirable alterations in the binding characteristics of the ligand. A radioactively labeled binding assay is popular for membrane based targets; however, the assay suffers from high cost along with hazards of handling high levels of radioactivity and thus comes with many restrictions for the lab and lab personnel working with the assay. NMR based analysis has also been applied to analyze the detailed structure of proteins and thus to assist in structure based drug design but suffers from a high cost of the assay and a long time required to analyze the spectra.

A previously developed thermal shift assay, also called differential scanning fluorimetry (DSF), is a thermal-denaturation assay that measures the thermal stability of a target protein and a subsequent increase in protein melting temperature upon binding of a ligand to the protein. The thermal stability change is measured by performing a thermal denaturation curve in the presence of a fluorescent dye, such as Sypro Orange. Such methods also involve a step of centrifugation and oil dispensing.

Thus, there is a need for a binding assay that offers a facile, sensitive and precise detection of ligand protein interaction, in a homogeneous assay format.

SPECIFIC PATENTS AND PUBLICATIONS

U.S. Pat. No. 6,020,141, "Microplate thermal shift assay for ligand development and multi-variable protein chemistry optimization," issued Feb. 1, 2000 to Pantoliano et al., discloses a thermal shift assay that comprises contacting the target molecule with one molecule of a multiplicity of different molecules in each of a multiplicity of containers, simultaneously heating the multiplicity of containers, and measuring in each of the containers a physical change associated with the thermal denaturation of the target molecule.

Jung et al., "Affinity Map of Bromodomain Protein 4 (BRD4) Interactions with the Histone H4 Tail and the Small Molecule Inhibitor JQ1," J. Biol. Chem. Feb. 2, 2014, 289:9304-9319 discloses a thermal shift assay where BRD4 BD1 protein was mixed with 5 µl Sypro Orange (Molecular Probe).

BRIEF SUMMARY OF THE INVENTION

The following brief summary is not intended to include all features and aspects of the present invention, nor does it imply that the invention must include all features and aspects discussed in this summary.

The present invention comprises a method of measuring binding of a test compound to a target macromolecule. Further, the present invention discloses a homogeneous method of measuring binding of a test compound to a target protein of interest under heat denaturation of a macromolecule having a defined, native secondary and, optionally, tertiary structure, wherein the denaturation disrupts the secondary and/or tertiary structure of the target protein, but not a labelling peptide attached to it. The method may therefore be carries out in a homogenous format, without centrifugation or filtration steps between addition of the sample and reading out a result. The method will cause a lack of solubility and accessibility of the labeling peptide attached to the target macromolecule; the labeling peptide may conveniently be added at the N or C terminus of the protein-based macromolecule. As will be described below, a number of short, relatively low temperature heat pulses are preferred to a single heat step; similarly, it is not preferred to completely melt a protein under study.

In one embodiment, the present methods comprise a method for carrying out an assay for binding between a compound and a target macromolecule, comprising: (a) preparing a fluid mixture comprising (i) a chimeric molecule comprising a target macromolecule linked to a labeling peptide and (ii) a compound being measured for binding to the target macromolecule, wherein said target macromolecule is subject to denaturation; (b) permitting binding of said compound to said target macromolecule; (c) treating a mixture of step (b) with an agent that denatures target macromolecules under conditions (e.g., time and temperature) in which a lesser degree of denaturation occurs to target macromolecules bound to the compound compared to denaturation of target macromolecules bound to the compound; and (d) detecting a signal from target macromolecules bound to the compound in step (c) by adding to the mixture a second label that reacts with the labeling peptide, whereby, a signal is generated that is modulated by the denaturation.

In certain embodiments, the present invention comprises a method for measuring a binding property between a compound and a target macromolecule, comprising: (a) preparing a fluid mixture comprising (i) a chimeric molecule comprising a target macromolecule subject to denaturation linked to a labeling peptide and (ii) a compound being measured for binding to the target macromolecule; (b) incubating the fluid mixture of step (a) under conditions permitting binding of said compound to target macromolecules in the mixture; (c) treating the fluid mixture of step (b) under conditions that cause a differential denaturation between chimeric molecules bound to the compound and chimeric molecules not bound to the compound; and (d) generating a signal from chimeric molecules subjected to said differential denaturation in step (c), by adding to the mixture a second label that reacts with the labeling peptide in the chimeric molecule, wherein, (e) the signal in step (d) is detected and indicates a binding property between the compound and the target macromolecule.

As explained below, the present invention as described above may be combined with a variety of steps and features described below. In certain embodiments, the invention comprises a step wherein detecting a signal indicates a differential between (i) denatured and (ii) non-denatured target macromolecules and thereby a differential between target macromolecules not bound to the compound and target macromolecules bound to the compound, respectively.

In one embodiment, the method comprises preparing a chimeric molecule that is a fusion protein comprising a labeling peptide and a protein target macromolecule. In another embodiment, the method comprises preparing a fusion protein comprising a nucleotide binding domain, labeling peptide and a target macromolecule. The nucleotide binding domain may be a DNA binding domain. The target macromolecule may be a protein, a peptide, a carbohydrate or a lipid molecule.

In one embodiment, the method comprises incubating the fusion protein (target macromolecule) with a test compound under binding conditions that may evaluate the binding of the test compound to the fusion protein. In another embodiment, the incubation is followed by heating the mixture gradually, and/or applying separate heating steps to accomplish a pulse denaturation of the target macromolecule.

In some embodiments, the method comprises constructing a fusion protein comprising a DNA binding domain within the target macromolecule and a labeling peptide; incubating the target macromolecule with a test compound under binding conditions; heating the mixture gradually; introducing a binding partner of the labeling peptide and measuring the signal wherein the signal indicates binding between the test compound and target macromolecule. In other embodiments, the method comprises constructing a fusion protein comprising a target macromolecule and a labeling peptide; incubating the fusion protein with a test compound under binding conditions; heating the mixture gradually; introducing a binding partner of the labeling peptide and measuring a signal wherein the signal indicates binding between the test compound and target macromolecule. In some embodiments, a control is also run in parallel, wherein the test compound is not introduced into the mixture and a signal is measured.

In some embodiments, the target macromolecule may be a protein, a peptide, a carbohydrate, a nucleotide or a lipid molecule. The target macromolecule may be denatured by heat or other, physical, means.

In some embodiments, a method comprises a measurement that is effected by the tertiary structure of the target macromolecule. It comprises a measurement of a signal generated by enzyme fragment complementation (EFC) wherein two or more than two fragments of β-galactosidase complement each other to form an active enzyme which can act on a substrate to give a measurable product. The labeling peptide is a small fragment of β-galactosidase such as an enzyme donor (ED) and the binding partner of the labeling peptide is a large fragment of β-galactosidase such as an enzyme acceptor (EA). The ED and EA fragments of β-galactosidase are inactive as individual fragments but possess affinity for each other. When they come in close vicinity to one another, the fragments complement each other and form an active β-galactosidase enzyme.

In some embodiments, the test compound may be a small molecule, an inhibitor, an allosteric modulator, or another synthetic compound.

In some embodiments, the labeling peptide is a fluorescent protein fragment, where fluorescent properties are restored when the complementary fluorescent protein fragment is present together with it. See, e.g., Ferrara F, Listwan P, Waldo G S, Bradbury A R M (2011) Fluorescent Labeling of Antibody Fragments Using Split GFP. PLoS ONE 6(10): e25727. doi:10.1371/journal.pone.0025727.

In some embodiments, of the present invention, the above-described heat denaturation is carried out over a predetermined series of short heat pulses followed by short re-equilibration at room temperature or below. The short heat pulses may be at a temperature that is below the melting temperature of the protein being heat denatured. In some embodiments, re-equilibration is facilitated by the use of a Peltier device that provides thermoelectric heating and cooling.

In certain embodiments, the present invention comprise a method for measuring a binding property (e.g. $K_D$) between a compound and a target macromolecule, comprising: (a) preparing a fluid mixture comprising (i) a chimeric molecule comprising a target macromolecule subject to denaturation linked to a labeling peptide and (ii) a compound being measured for binding to the target macromolecule; (b) incubating the fluid mixture of step (a) under conditions permitting binding of said compound to macromolecules in the mixture; (c) treating the fluid mixture of step (b) under conditions that cause denaturation of macromolecules not bound to the compound and also cause less denaturation of macromolecules bound to the compound; and (d) detecting a signal from macromolecules bound to the compound in step (c) by adding to the mixture a second label that reacts with the labeling peptide on bound macromolecules, whereby, the second label binds to the labeling peptide to create a detectable signal if the compound has bound to a macromolecule and is not denaturation, and whereby the signal is generated only of the second label reacts with the labeling peptide. This binding property may be measured in replicate to determine a binding association in a dose dependent way.

In certain embodiments, the present invention comprises a method as described below and/or in combination with an embodiment described below, wherein said conditions that cause denaturation comprise heating and cooling steps. Cooling steps may be accomplished by discontinuation of heating. In certain embodiments, the present invention comprises a method as described below and/or in combination with an embodiment described below wherein the target macromolecule is a protein or protein fragment. In certain embodiments, the present invention comprises a method as described below and/or in combination with an embodiment described below wherein the labeling peptide is between 10 and 100 amino acids in length. In certain embodiments, the present invention comprises a method as described below and/or in combination with an embodiment described below wherein the labeling peptide is an enzyme fragment and the second label is a complementary enzyme fragment which combined with the labeling peptide to create an active enzyme when not inhibited by denaturation. In certain embodiments, the present invention comprises a method as described below and/or in combination with an embodiment described below wherein the labeling peptide is an enzyme donor ("ED") having a sequence active in enzyme fragment complementation of β-galactosidase fused to a terminus of the target macromolecule. In certain embodiments, the present invention comprises a method as described below and/or in combination with an embodiment described below wherein the ED is one of SEQ ID NO: 1, SEQ ID NO: 2, SEQ ID NO: 3, or SEQ ID NO: 4. In certain embodiments, the present invention comprises a method as described below and/or in combination with an embodiment described below wherein the labeling peptide is an epitope tag. In certain embodiments, the present invention comprises a method as described below and/or in combination with an embodiment described below wherein the compound is a small molecule. In certain embodiments, the present invention comprises a method as described below and/or in combination with an embodiment described below wherein the small molecule is one that binds to an active site on the target macromolecule.

In certain embodiments, the present invention comprises a method as described below and/or in combination with an embodiment described below wherein said the conditions that cause denaturation of macromolecules comprises the step of heating at a defined temperature that is one of between 25° C. to 100° C., or between 30° C. and 50° C. In certain embodiments, the present invention comprises a method as described below and/or in combination with an embodiment described below wherein said heating is for a defined period of time between 0.1 and 5 minutes. In certain embodiments, the present invention comprises a method as described below and/or in combination with an embodiment described below wherein said heating step comprises applying heat to the mixture between 40° C. and 45° C., and further comprises a total heating time of 2 to 5 minutes, said total heating time being interspersed between times with no heating. In certain embodiments, the present invention comprises a method as described below and/or in combination with an embodiment described below said heating step comprises cooling periods of 30 seconds to 2 minutes, or 10 seconds to 2 minutes. In certain embodiments, the present invention comprises a method as described below and/or in combination with an embodiment described below comprising 3 to 10 cooling periods.

In certain embodiments, the present invention comprises a method as described below and/or in combination with an embodiment described below wherein said cooling periods reach at least ambient temperatures. In certain embodiments, a series of heating and cooling steps are carried out where the cooling step simply involves depowering a heat source, while the actual temperature in the mixture does not return to ambient (room) temperature, but gradually accumulates heat from previous heating step(s). In certain embodiments, the present invention comprises a method as described below and/or in combination with an embodiment described below wherein said cooling periods comprise actively cooling the mixture.

In certain embodiments, the present invention comprises a method as described below and/or in combination with an embodiment described below wherein the step of denaturation comprises the addition of a strong acid or base, a concentrated inorganic salt, an organic solvent, or exposure to radiation. In certain embodiments, the present invention comprises a method as described below and/or in combination with an embodiment described below wherein the organic solvent is alcohol or chloroform.

In certain embodiments, the present invention comprises a method as described below and/or in combination with an embodiment described below wherein steps of preparing a fluid mixture, incubating, treating under conditions to cause denaturation, an detecting a signal may be used to calculate a characteristic of the binding of compound to the target macromolecule.

In certain embodiments, the present invention comprises a method as described below and/or in combination with an embodiment described below the target macromolecule is a protein which is one of a bromodomain protein, a protein kinase or a histone methyltransferase.

In certain embodiments, the present invention comprises a method as described below and/or in combination with an embodiment described below a method for preparing an assay mixture useful for measuring a binding property between a compound and a target macromolecule, comprising: (a) preparing a fluid mixture comprising (i) a chimeric molecule comprising a target protein subject to denaturation linked to a labeling peptide that is a β-galactosidase enzyme fragment of between 10 and 100 amino acids in length and (ii) a small molecule being measured for binding to the target protein; (b) incubating the fluid mixture of step (a) under conditions permitting binding of said compound to proteins in the mixture; and (c) heating the fluid mixture of step (b) under conditions that cause denaturation of proteins not bound to the compound and also cause less denaturation of proteins bound to the compound, whereby one may detect a signal from proteins bound to the compound in step (c) by adding to the mixture a second label that is a β-galactosidase fragment that reacts with the labeling peptide on bound protein. In certain embodiments, the present invention comprises a method as described below and/or in combination with an embodiment described below the assay mixture is prepared through steps (a) to (c) in a single container. In certain embodiments, the present invention comprises a method as described below and/or in combination with an embodiment described below replicate samples containing different concentrations of compound are prepared.

In certain embodiments, the present invention comprises a method as described below and/or in combination with an embodiment described below wherein is prepared a fluid mixture comprising a target macromolecule fused to an enzyme donor, wherein a fraction of the fused target macromolecule is insoluble and not bound to a binding compound, and a remaining fraction is soluble and bound to the binding compound, said composition further comprising an enzyme donor.

In certain embodiments, the present invention comprises a kit comprising instructions for measuring binding of a potential ligand to a target protein, said kit and instructions comprise: (a) preparing a fluid reaction mixture comprising (i) a target protein fused at a terminus to a first β-galactosidase enzyme fragment, and (ii) the potential ligand to the target protein; (b) instructions for heating the reaction mixture of step (a) to cause at least a partial melting of the target protein; (c) instructions for measuring, in the reaction mixture, after step (b), the amount of fusion protein that is not denatured in step (b), by adding to the mixture a β-galactosidase enzyme fragment that is commentary to the first β-galactosidase enzyme fragment, and a substrate that indicates complementation of the β-galactosidase enzyme and indicates binding of the potential ligand as an inverse function of the heat step of step (b). In certain embodiments, the present invention further comprises a kit wherein said substrate is colorimetric, fluorometric or chemiluminescent with active β-galactosidase but not inactive β-galactosidase. In certain embodiments, the present invention comprises a kit wherein the first β-galactosidase enzyme fragment is essentially identical to one of SEQ ID NO: 1, SEQ ID NO: 2, SEQ ID NO: 3 or SEQ ID NO: 4.

In one embodiment, the pulse heating may be carried out by a programmable thermal cycler. In another embodiment, the pulse heating may be carried out by an instrument capable of sending short heat pulses for a specific time and at a specific temperature.

BRIEF DESCRIPTION OF THE DRAWINGS

FIG. 8A, 8B is pair of graphs showing an example of a pulse-denaturation protocol. FIG. 8A shows a standard denaturation profile of 1 cycle, with a high temperature (45° C.) over a time period of 3 minutes; FIG. 8B shows a pulse denaturation profile of 25 pulses at a reduced temperature of 40° C., where each pulse represents a brief denaturation pulse time of 7 seconds (i.e. a period of heating that is 7 seconds), where a PCR thermal cycler is reset to a lower temperature (e.g. ambient temperature) after a heating pulse.

Protein samples were exposed to a standard single heat denaturation step ("standard") or to repetitive 0.5 minute heat pulses. A 45° C. denaturation temperature was used for both protocols. "Total denaturation time" is the total amount of time that the protein sample was exposed to 45° C., so one single 3 minute step with the standard protocol (i.e. no pulsing, but a single 3 minute heating step at a constant temperature) is equivalent to 6 repetitive 0.5 minute steps with the pulse protocol. That is, six 0.5 heat pulses may be compared to one 3 minute heating step.

Figure 11:
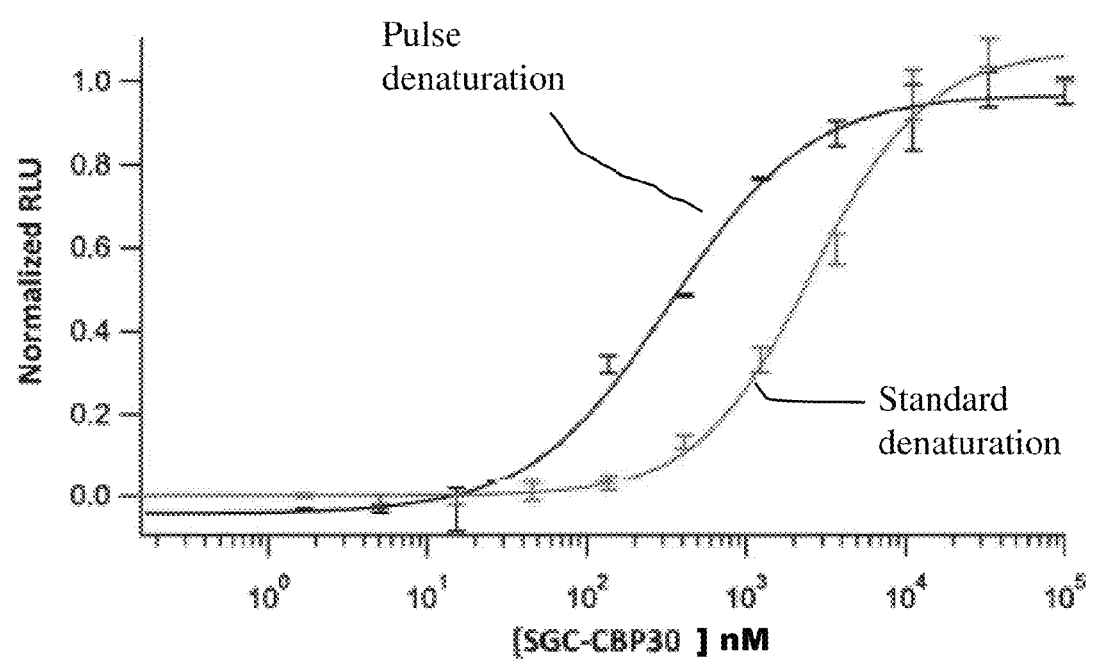

FIG. 11 is a graph showing different signals in RLU (relative luminosity units) comparing pulse denaturation versus standard denaturation for binding of SGC-CBP30 (a CREBBP/EP300-selective chemical probe), present at different concentrations, to CREBBP (Gene ID 1387, NCBI). SGC-CBP30 is commercially available from Tocris Biosciences, and is 8-(3-chloro-4-methoxy-phenethyl)-4-(3,5-dimethyl-isoxazol-4-yl)-9-(2-(morpholin-4-yl)-propyl)-7,9-di-aza-bicyclo[4.3.0]nona-1(6),2,4,7-tetraene. Dose response curves were measured for CREBBP with SGC-CBP30 with the "standard protocol" at 45° C. or with the "pulse protocol" at 40° C. Multiple cycles of gentle denaturation at 40° C. yielded EC50 values closer to the $K_D$ of 0.021 µM measured by Isothermal Titration calorimetry (see description of isothermal titration calorimetry in Picaud et al. "RVX-208, an inhibitor of BET transcriptional regulators with selectivity for the second bromodomain," PNAS Dec. 3, 2013 vol. 110 no. 49: 19754-19759). The gentle denaturation is less than the melting point of CREBBP, which is 46° C.

Figure 12:
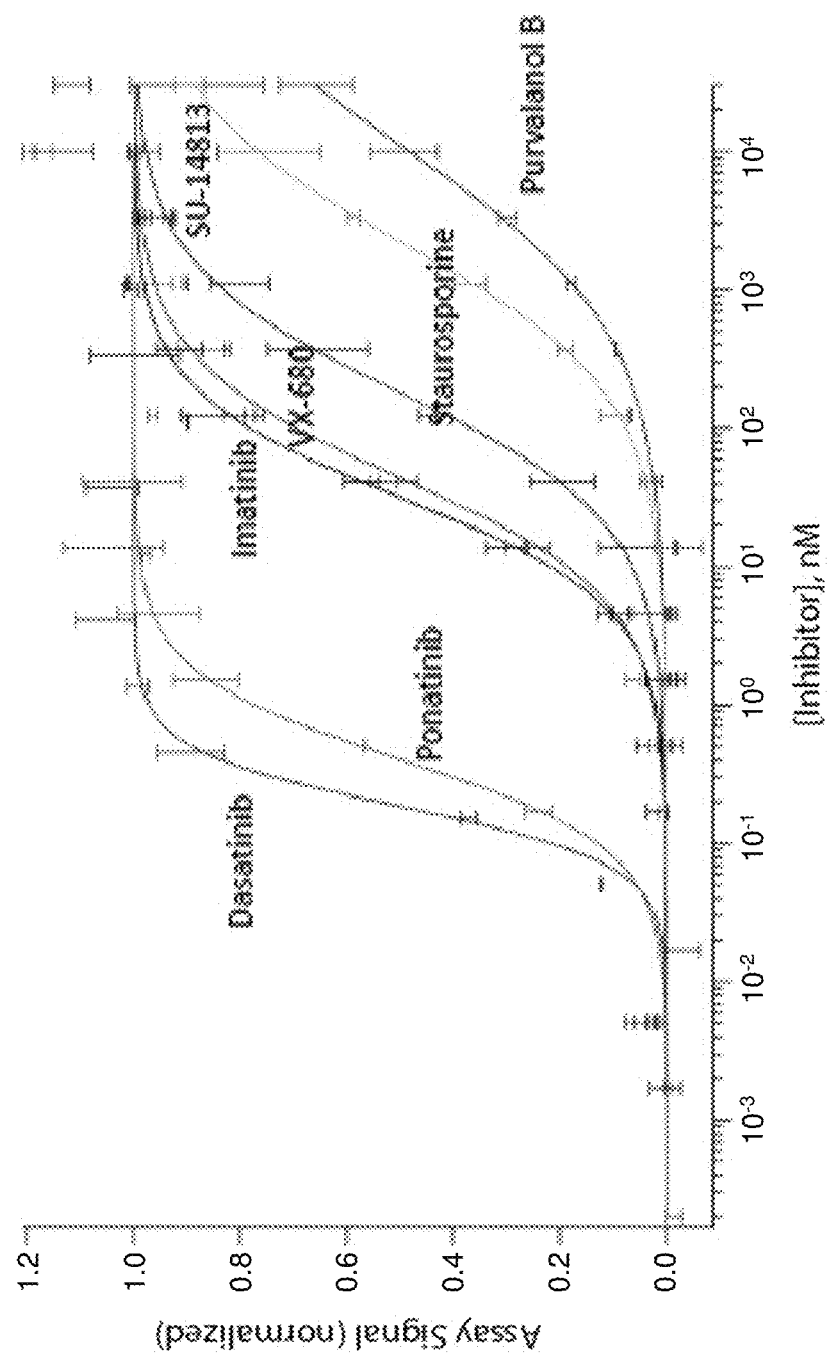

FIG. 12 is a graph showing dose response curves for seven inhibitors of the ABL1 protein kinase. The dose response curves were obtained using ED-tagged ABL1 and the inhibitors in a pulse denaturation protocol. It shows, for example, that one compound tested, dasatinib (N-(2-chloro-6-methylphenyl)-2-[[6-[4-(2-hydroxyethyl)-1-piperazinyl]-2-methyl-4-pyrimidinyl]amino]-5thiazolecarboxamide, monohydrate), binds to the test protein, ABL1, to a significant degree at a 1 nM concentration, whereas other compounds, such as imatinib (4-[(4-methylpiperazin-1-yl) methyl]-N-[4-methyl-3-[(4-pyridin-3-ylpyrimidin-2-yl) amino]phenyl]benzamide), do not bind at 1 nM to a significant effect, as measured by the present heat pulse assay. Very significant differences among different inhibitors were easily visualized.

Figure 13:
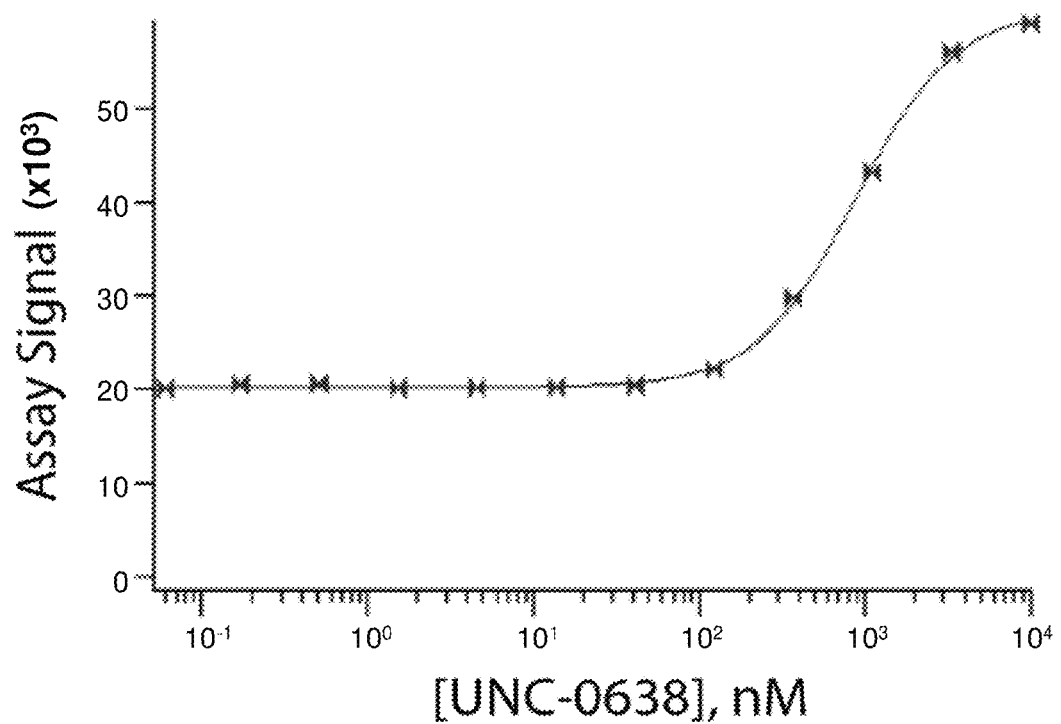

FIG. 13 is a graph showing a dose response curve for UNC-0638 (2-Cyclohexyl-6-methoxy-N-[1-(1-methylethyl)-4-piperidinyl]-7-[3-(1-pyrrolidinyl)propoxy]-4-quinazolinamine), an inhibitor of the G9a protein methyltransferase. The dose response curve was obtained using ED-tagged G9a and the inhibitor in a pulse denaturation protocol.

DETAILED DESCRIPTION

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A laboratory Manual (1982); "DNA Cloning: A Practical Approach, "Volumes I and II (D. N. Glover ed. 1985); "Oligonucleotide synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide to Molecular Cloning" (1984).

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

Ranges: For conciseness, any range set forth is intended to include any sub-range within the stated range, unless otherwise stated. As a non-limiting example, a range of 2 minutes to 8 minutes includes 3-4 minutes, 2-7 minutes, etc. A temperature range of 40-45° C. includes 41-45° C., 42-43° C., etc. The term "about" has its ordinary meaning of approximately and may be determined in context by experimental variability. In case of doubt, the term "about" means plus or minus 5% of a stated numerical value.

As will be apparent to those of skill in the art upon reading this disclosure, each of the individual embodiments described and illustrated herein has discrete components and features which may be readily separated from or combined with the feature of any of the other several embodiments without departing from the scope or spirit of the present invention. Any recited method can be carried out in the order of events recited or in any other order which is logically possible.

The term "peptide" as used herein refers to any polymer compound produced by amide formation between an α-carboxyl group of one amino acid and an α-amino group of another group. As used herein, a peptide may be a labeling peptide, of relatively small size, having little or no secondary structure (i.e. a loop) linked to a macromolecule and for detecting the fusion.

The term "protein" as used herein refers to polypeptides of specific sequence of more than about 50 residues. While all proteins are peptides, the term "peptide" generally refers to a fragment of a protein; the term "fusion protein" is used to refer to both fusion proteins and fusions with peptides, such as a fusion with a labeling peptide, e.g. an ED. In connection with the present assay, it will be understood that the protein under study need not be a fill length protein sequence. The target macromolecule may in fact be a protein that has been truncated to isolate a domain under study, modified for easier handling, etc. Thus a protein fragment in the present assay is referred for simplicity as a "protein".

The term "fusion protein" as used herein refers to a protein created through genetic engineering from two or more proteins/peptides. In general, this is achieved by creating a "fusion gene", a nucleic acid that encodes the fusion protein. For example, a fusion gene that encodes a fusion protein may be made by removing the stop codon from a first DNA sequence encoding the first protein, then appending a DNA sequence encoding the second protein in frame. The resulting fusion gene sequence will then be expressed by a cell as a single fusion protein. Fusion proteins may include a linker (or "spacer") sequence which can promote appropriate folding and activity of each domain of the fusion protein. Fusion proteins may also include epitope tags (labeling peptide) for identification (e.g., in western blots, immunofluorescence, etc.) and/or purification. Non-limiting examples of epitope tags in current use include: HA, myc, FLAG, and 6-HIS. These known epitope tags are relatively short peptides that can be specifically detected by monoclonal antibodies, i.e. a second label that binds to the epitope tag attached to the target macromolecule.

The fusion protein will be "chimeric" if the molecule contains two sequences that are not normally found together in the same polypeptide chain. A chimeric molecule may also contain a fusion of two different polymers, such as a single polypeptide chain comprising the target macromolecule and the labeling peptide. The chimeric molecule may also contain a labeling peptide chemically linked to the target macromolecule.

For purposes of the present invention, a protein used in the assay will often be a human protein of interest as a drug target, and will be prepared by recombinant methods in an active form and containing known protein binding sites. However, the present definition of "protein" specifically includes fragments of proteins that are not full length proteins, but contain only a fragment of sufficient structure to have the requisite secondary structure and have the binding site to the compound of interest.

The term "target macromolecule" as used herein refers to various macromolecules that can be denatured. That is, they have a secondary or tertiary structure that can be eliminated by heat, or, alternatively, other agents. They are, for example DNA, RNA, proteins and or their constituent oligomers. In some cases, the "macromolecule" may be of a relatively small MW compared to a full length protein, provided that it has a native three dimensional structure that is rigidly defined by cross linking, hydrogen binding or the like. For example, knottin small peptides have a rigid, defined tertiary structure that could be measured by the present assay. The term "macromolecule" refers to a polynucleotide, polypeptide or a complex carbohydrate having a defined tertiary structure. For example, glycans, often present as glycoproteins or glycolipids, form highly complex structures. In mammals ten monosaccharides are utilized in building glycoconjugates in the form of oligo- (up to about a dozen monomers) and polysaccharides. The present "macromolecule" is one that can be denatured by destroying in significant part such three dimensional structure. A "target" macromolecule is a macromolecule capable of binding specifically to a third molecule, typically a small molecule or other pharmaceutical drug candidate. The target macromolecule used in the present assays may be purified, present in a cell extract, or in other forms.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a synthetic or purified natural small molecule that is often identified as being an organic or medicinal compound, and does not include molecules that contain nucleic acids, peptides or polypeptides.

The term "binding" as used herein refers to the binding of small molecules, proteins or compounds to the proteins in a cell or in a solution. The terms "binding partner" or "member of a binding pair" refer to molecules that specifically bind other molecules to form a binding complex such as antibody-antigen, lectin-carbohydrate, nucleic acid-nucleic acid, biotin-avidin, etc. In particularly preferred embodiments, the binding is predominantly mediated by non-covalent (e.g. ionic, hydrophobic, etc.) interactions and is between a small molecule and its target and/or two proteins that specifically bind to each other during a cellular process.

The term "Enzyme fragment complementation (EFC)", as explained below involves the use of one enzyme fragment, which may be referred to as a labeling peptide or an ED (enzyme donor), which is not enzymatically active until it is complexed with another enzyme fragment, termed an EA, or enzyme acceptor, or second label. The terms ED and EA are used with reference to β-galactosidase. However, the term EFC or labeling peptide is not limited to a β-galactosidase system. EFC is a generic term to describe the combination of enzyme fragments to form active enzyme, followed by detection of that activity by measurement of a hydrolysis product, generally by colorimetric, fluorometric or chemiluminescent methods. It has the advantage of providing an amplification step, due to enzyme turnover, as part of the detection system.

By way of illustration, EFC assays based either on dihydrofolate reductase or beta-lactamase have been used to quantify the effects of the drug rapamycin on its target in living cells (Remy, I. and Michnick, S. W., Clonal Selection and In Vivo Quantitation of Protein Interactions with Protein Fragment Complementation Assays. Proc Natl Acad Sci USA, 96: 5394-5399, 1999; Galarneau, A., Primeau, M., Trudeau, L.-E. and Michnick, S. W., A Protein fragment Complementation Assay based on TEM1 β-lactamase for detection of protein-protein interactions, Nature Biotech. 20: 619-622, 2002) and to study phosphorylation-dependent interactions of two domains of the cyclic AMP response element binding protein, CREB (J M Spotts, R E Dolmetsch, & M E Greenberg, 2002, Time-lapse imaging of a dynamic phosphorylation-dependent protein-protein interaction in mammalian cells, Proc. Natl. Acad. Sci. USA 99: 15142-15147.).

The term "labeling peptide" means a peptide having essentially no secondary structure (i.e. random coil) and which functions as a label for detection of a protein or protein fragment (e.g. target peptide) fused thereto and having essentially no effect on the stability of the target peptide to which it is fused. The labeling peptide will generally be less than 100 amino acids in length. It may itself function as a label, or it may provide an epitope for antibody recognition. As explained below, the labeling peptide is selected so as not to affect the stability of a fusion partner of the labeling peptide.

The term "ED", as is known in the art, means an enzyme donor fragment for use in a β-galactosidase enzyme fragment complementation assay. Examples of EDs are given below. An ED that is "essentially identical to one of SEQ ID NO: 1-4 will be identical except of up to two amino acid alterations.

The term "EA", as is known in the art, means an enzyme acceptor fragment for use in a β-galactosidase enzyme fragment complementation assay.

The term "denaturation" is used in its conventional sense to refer to a process in which proteins, nucleic acids or other macromolecules or macromolecular structures (e.g. ribosomes) lose the quaternary structure, tertiary structure and or secondary structure, at least in part. Loss of this native state in the present method occurs by application of some external stress or compound such as a strong acid or base, a concentrated inorganic salt, an organic solvent (e.g., alcohol or chloroform), radiation or heat. The term used here specifically includes partial denaturation, where only a fraction of the molecules (e.g. proteins) in a mixture are denatured. The term protein "melting," which refers to protein denaturation, is also used herein. As is known, a melting temperature (Tm) may be determined from a protein denaturation study. See, for details, US 20130217137.

The term "pulse denaturation" refers to a process in which proteins or nucleic acids denature by application of more than one cycle of a short heat pulse at a mild temperature which is followed by short re-equilibrium at room temperature or below room temperature. A "mild temperature" is considered to be a temperature at least about 5° C. less than the melting temperature of the macromolecule being heated. A protein melting point can be determined by known methods, as in e.g. US 20140057368, referred to below. A pulse denaturation protocol may cause a small amount of denaturation in a given step (5%-10%). However the denaturation is cumulative over multiple cycles, and may reach 80% of more denaturation after the pulses are applied. By way of example, a pulse denaturation protocol may comprise 10-70 pulses at 37-50 deg. C. for 5-10 seconds, separated by 15-20 second cooling pulses.

The term "protein denaturation" refers to denaturation of proteins involving the disruption and possible destruction of both the secondary and tertiary structures.

Denaturation disrupts the normal alpha helix and beta sheets in a protein and uncoils it into a random shape resulting in precipitation or coagulation of the protein. Denaturation of proteins results in loss of their biological function and/or activity. Denaturation may occur by some external stress or compound such as a strong acid or base, a concentrated inorganic salt, an organic solvent, radiation, heat or cold. Denaturation can be complete or partial but, for the present purposes, is sufficient to cause insolubility.

The term "thermal stability" refers to a quality of a macromolecule such as a protein to resist irreversible change in its chemical or physical structure at a high relative temperature.

The term "thermal shift assay" refers to an assay based on the principles that a purified protein will denature and unfold at a particular temperature and that the binding of a ligand to a protein will thermally stabilize the protein. Further details on carrying out various thermal shift assays may be found in Nordlund, US 20140057368, "Methods for determining ligand binding to a target protein using a thermal shift assay." As described there, such assays may be carried out with non-purified samples.

The term "homogenous" is used in its standard sense, to refer to an assay format and method that does not require a separation step. This allows measurement of results by a simple mix and read procedure, without the need to process samples by separation or washing steps during the assay.

Overview

The present method monitors and measures a binding property between a compound and a macromolecule. It exploits the known ability of ligands such as small molecules to protect macromolecules such as proteins from denaturation and precipitation due to unfolding. Prior art methods have required high-g-force centrifugation steps and insensitive readouts. The present methods, exemplified by the use of β-galactosidase enzyme fragment complementation, utilize a small peptide (less than 100 amino acids) fused to the macromolecule. The small peptide may be the known enzyme donor, the Prolabel™ ("ED") commercially available from DiscoveRx Corporation, Fremont Calif. Enzyme fragment complementation provides a sensitive, facile generic readout. Moreover, the assay may be carried out in a homogeneous format, meaning that no physical separation of the reagents is required, eliminating the need for filtration, decanting, centrifugation, etc. The present invention is widely applicable to a number of ligand binding assays.

The ligand may typically be a small molecule that is under study for binding properties to a target molecule, which will be a macromolecule that is susceptible to thermal denaturation and resultant loss of buoyancy or solubility in a fluid. The binding property may be measured in the presence of a competitor or under different target macromolecules. The invention is illustrated, but not limited, by a study of BRD4 (bromodomain-containing protein 4). As demonstrated here, the present methods provide:

1. Generic homogeneous direct ligand binding assay;
    Simple, rapid method (no wash, filtration, or centrifugation steps)
    No protein purification required brd4
    No fluorescent labels or antibodies
    Target protein present at <10 nM
    Exploits DiscoveRx's proprietary Enzyme Fragment Complementation (EFC) technology
2. BRD4(1) working example
    Highly precise (median % CV (coefficient of variance ~0.5); outstanding signal to noise ratio
    Correct rank order for high and low potency inhibitors
3. Applications
    High throughput screening (384-well compatible)
    Hit confirmation & potency rank order
4. Target classes
    Bromodomains; proteins of pharmaceutical interest, such as kinases, G protein-coupled receptors, methyltransferases, RAS, MAPK, and MSK1 signaling molecules, nuclear receptors, ion channels, etc. Preferred target classes are human drug targets.

Figure 1:
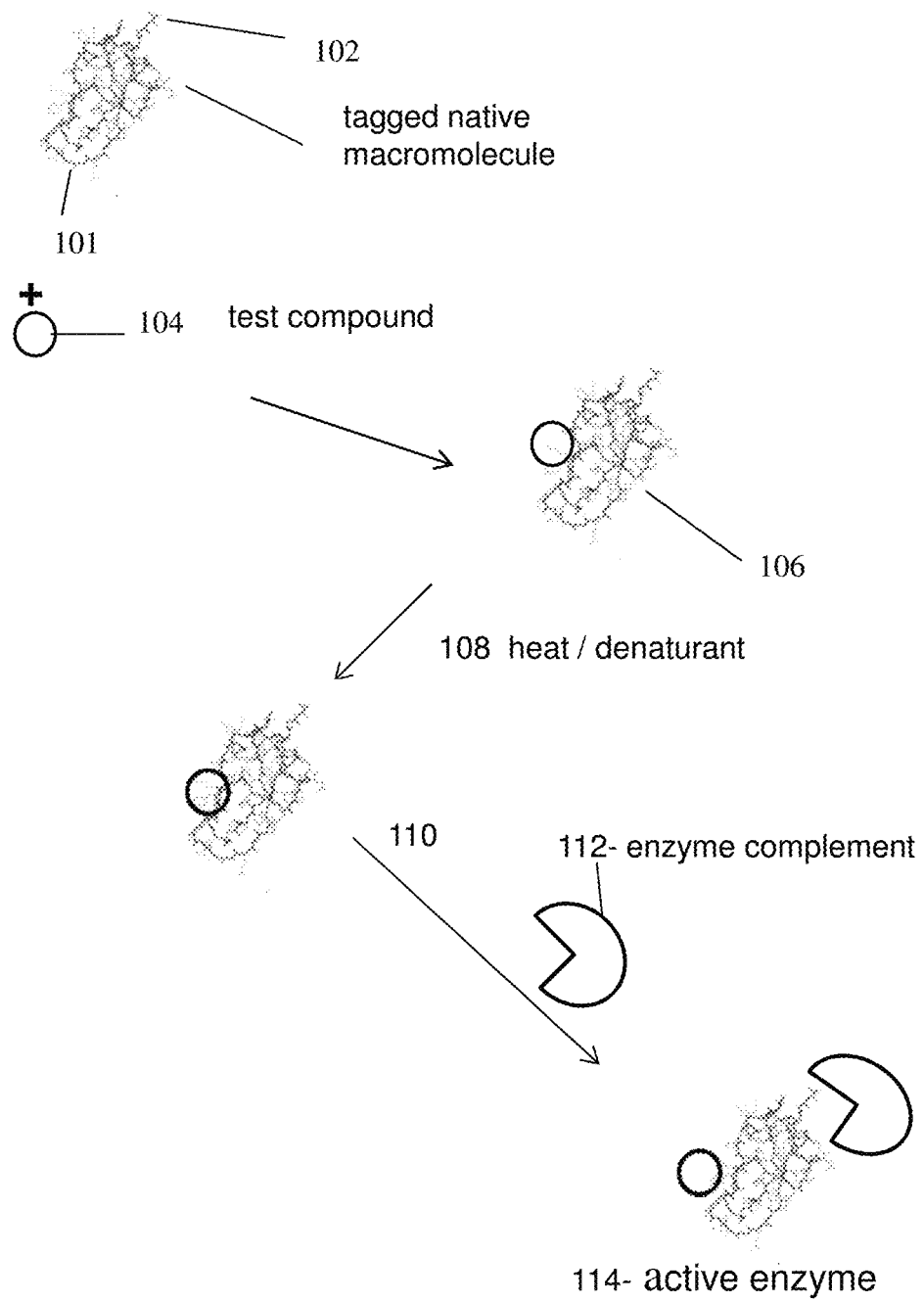
FIG. 1 is a schematic representation of the present assay showing how a tagged macromolecule (e.g. a fusion protein/nucleic acid and labeling peptide) is in native form (i.e. native secondary and tertiary structure) protected from denaturation in the presence of a test compound that binds to the tagged native macromolecule; the protection therefore enables detection of the binding with an enzyme complementation assay.
Figure 2:
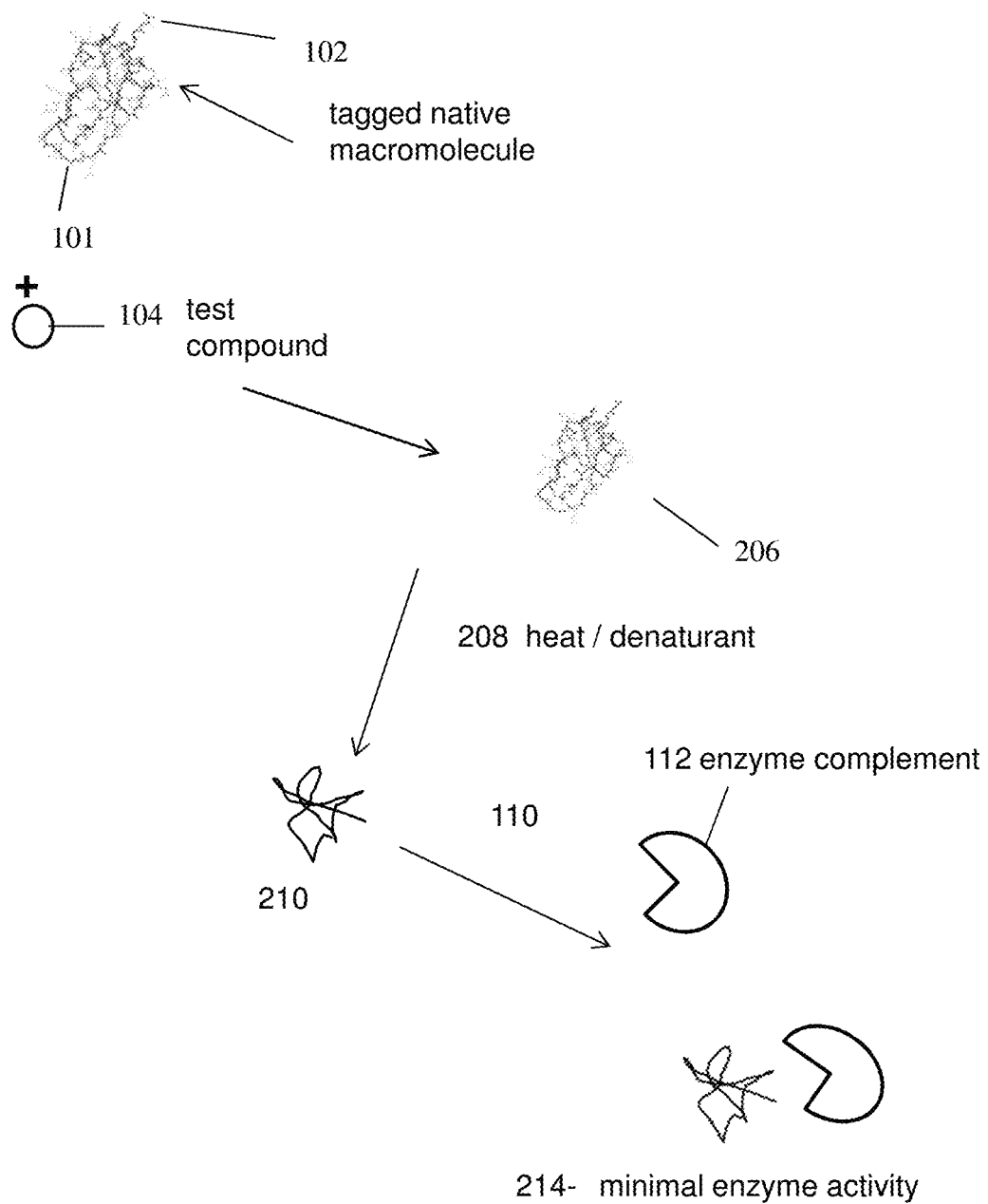
FIG. 2 is a schematic representation of the assay principle as in FIG. 1, except that in this situation the test compound does not bind to the tagged native macromolecule, resulting in denaturation of the tagged native macromolecule and further making the tag (labelling peptide) inaccessible for complementation.

The present methods may also be carried out with a series of heating pulses separated by cooling. The heat applied to the above described mixture of proteins and (potential) ligands serves, as described above to denature the protein; the resulting activity may be measured as shown in FIGS. 1 and 2. That is, the described methods may include a pulsed denaturation protocol where protein samples (+/− ligand) are subjected to several cycles (e.g. 10-200 cycles) of a short heat pulse at mild temperature which is followed by short re-equilibration at room temperature or below. These "pulse" protocols are easily carried out by using standard programmable thermal cycler instrumentation. This method avoids the need for high denaturation temperatures and long denaturation times and therefore increases the sensitivity of the method for detection of inhibitor binding. Given the present teachings, one may routinely determine optimal heating times, cooling times, cooling temperatures, and heating temperatures. These will be based on the biophysical properties of the target macromolecule under study, which include the temperature at which fifty percent of the molecules have unfolded (this temperature is known as the melting temperature or $T_m$). Other factors considered will be the expected affinity of the test compounds, the concentrations under study, etc.

General Method

Proteins, among other macromolecules, are one of the most studied and most targeted macromolecules in the pharmaceutical industry. A number of approaches have been designed and invented to study proteins, their structure, their chemistry, protein-protein interactions, protein-test compound interactions, and biological pathways where proteins participate, and to determine small molecule binding to proteins of interest. However, all these processes and measurements require proteins to be stable and active as proteins are susceptible to degradation or aggregation by a number of factors.

Macromolecules such as proteins denature when exposed to high temperatures, leading to their precipitation and aggregation. Binding of a compound to a macromolecule can increase its thermal stability and hence can be explored for a binding assay wherein one can measure a target macromolecule binding to a macromolecule by measuring its thermal stability. Thus, a compound that binds at an active or allosteric site of a macromolecule such as a protein will form a complex and influence its thermal stability. This will lead to the compound being stable even at higher temperatures. As known, a thermal shift assay measures the thermal stability of a target protein and a subsequent increase in protein melting temperature upon binding of a ligand to the protein. A number of assays have been designed to study the thermal stability of proteins and investigate buffer conditions, ligands, co-factors, drugs and other compounds affecting this stability to identify protein complexes and further characterize them. An alternative format has also been disclosed to measure ligand binding to a target protein using a thermal shift assay. The assay works on both purified and non-purified protein samples even at a low concentration. However, the assay requires that denatured, precipitated proteins be removed by centrifugation and stabilized proteins be quantified by low dynamic range immune-assays such as Western blot or ELISA.

Thus, there is still a lack of a simple, sensitive, high throughput and precise readout assay to determine ligand binding in extracts, cells and tissues.

The present invention discloses a homogeneous binding assay to determine ligand macromolecule interactions, and further, how these interactions result in stabilization of the macromolecule. More specifically, the present invention discloses a homogeneous binding assay to determine ligand protein interactions, and further, how these interactions result in stabilization of the protein under heat stress.

Referring now to FIG. 1 and FIG. 2, a macromolecule 101 having a secondary or tertiary structure is linked chemically to a tag 102, which may be an enzyme fragment and may be a fusion protein with a protein macromolecule. A test compound 104 is mixed in a fluid environment with the tagged native macromolecule under buffer and physical conditions that will allow the test compound to bind to the native macromolecule in a specific recognition being evaluated. Non-specific binding is minimized by the buffer conditions. The buffer may contain low concentrations of detergent (0.05% Tween 20). Nonspecific binding is also minimized because of all the other proteins in the crude extract that discourage non-specific binding. The binding of interest is generally of specific high affinity binding. The test compound may be binding to a specific binding site designed in nature to receive and bind a ligand. After this incubation, the test compound is allowed to bind to the chimeric molecule comprising the target macromolecule linked to the labelling peptide, as shown at 106. As shown at arrow 108, the heat denaturation step is applied to the construct in the mixture. Then, as shown at arrow 110, a complementary enzyme fragment 112 is added to the mixture and will complement the tag 102 on macromolecules in which denaturation was minimized by the binding of the test compound. As shown at 114, an enzyme substrate or substrate mixture is added to the active enzyme found in the mixture, and a colorimetric reaction is read using standard optical methods.

In FIG. 2, the corollary of the schematic of FIG. 1 is shown. Here, under similar conditions to those of FIG. 1, the test compound 104 does not bind to the macromolecule 101. The heat denaturation treatment in 208 causes the macromolecules in the mixture to form an insoluble mass 210. Insolubility increases with the degree of denaturation. Thus, when the enzyme fragment 112 is added at 110, no, or minimal active enzyme is produced, as indicated at step 214. The denaturation of a portion or all of the macromolecules effectively sequesters their tag 102, reducing the signal from the mixture.

The process of FIG. 1 and FIG. 2 may both occur at the same time in the same mixture and reaction. The degree of binding may be measured under different concentrations and/or in the absence or presence of binding inhibitors. In this case, the "test compound" may be a known binder, and the evaluation is that of a test inhibitor.

Macromolecules

The present invention provides an assay system for detecting macromolecule-ligand interactions following heat stress and denaturation, using EFC or fluorescent protein complementation. The macromolecule tested generally is a large molecule and is typically created by polymerization of smaller subunits (amino acids and nucleotides). Macromolecules of interest include polynucleic acids, proteins and carbohydrates, having defined three dimensional structures. The present macromolecules denature, i.e. lose their quartenary structure (sub units), tertiary structure and/or secondary structure by application of some external stress, such as an external compound, radiation or heat.

Labeling Peptide

A labeling peptide is attached to the target macromolecule which aids in the detection of macromolecule stability, compound binding to the macromolecule, inhibitors of compound macromolecule binding, and allosteric modulators, among other applications. A number of labeling moieties can be used to detect ligand macromolecule binding. β-lactamase-complementing reporter subunits as derived from β-lactamase can be constructed and utilized. Activity of the complementing β-lactamase can be detected using substrates for β-lactamase developed in the art which include a fluorescent donor moiety and a quencher, wherein the attached group is hydrolyzed off after the substrate enters the cell. Fluorescence energy transfer between the donor and quencher then can be monitored as an indicator of β-lactamase activity, as described in PCT WO 96/30540 published Oct. 3, 1996.

Green fluorescent protein (GFP): The protein is isolated from a marine organism and exhibits bright green fluorescence when exposed to light in the blue to UV range. GFP is tagged with a protein of interest, making a fusion protein which, upon binding to a compound that affects thermal stability of the protein, can then be measured using fluorescence microscopy.

A chromogenic peptide substrate can also be used wherein the enzymatic cleavage of the peptide p-nitro-aniline amid linkage in the chromogenic peptide substrate results in release of the chromophore p-nitroaniline. The reaction can be monitored spectrophotometrically.

Other labeling moieties include those in a ras-based recruitment system (RRS and SOS), a fusion-protein based system such as a yeast two hybrid system and the like. The labeling moiety can be coupled to the macromolecule of interest using any suitable method. The labeling moiety may be linked to the macromolecule of interest either directly or via a linker. Enzymes capable of catalyzing conversion of a substrate to a detectable reaction product, either directly or indirectly, such as beta-glucuronidase, alkaline phosphatase, peroxidase, luciferase and beta-galactosidase, may also be used as labeling moieties.

Beta-galactosidase (β-gal) is encoded by the *E. Coli* lacZ gene and can act as a labeling peptide. The enzyme activity can be monitored by different methods including live-cell flow cytometry and histochemical staining with a chromogenic substrate. The β-gal enzymes and its fragments (See U.S. Pat. No. 4,708,929) are required to have a number of characteristics. The fragments are substantially inactive individually, in that there is little, if any, background with only one fragment present in the presence of substrate. Secondly, the fragments have sufficient affinity for each other, that in the absence of other binding, e.g. by entities fused to the fragments, the fragments will combine to provide an active enzyme. The small fragment ("ED" or "PL") may be designed artificially and will not interfere with the biological activity of the gene or protein to which it is fused. The resulting fusion protein, as has been determined here, will fold properly and retain sites of activity, including enzyme activity, binding activity to other proteins, translocation capability, etc. The ED will usually be at least about 37, usually at least about 40 amino acids, and usually not more than about 110, more usually not more than about 90.

The β-galactosidase complementation system here is one that is made up of two or more β-galactosidase fragments or variants thereof. For example, in certain embodiments, the complementation system includes a first and second fragment of β-galactosidase (e.g., an α and ω fragment). In yet other embodiments, the complementation system may include more than two β-galactosidase fragments, such as a first, second and third β-galactosidase fragment (e.g., an α, β and ω fragment). In the present application, the small fragment of β-gal (also the signal producing peptide) will be referred to as the enzyme donor (ED). The signal producing peptide is one of a pair of fragments of an enzyme that is reconstituted when the two fragments, the enzyme donor ("ED") and the enzyme acceptor ("EA"), complex together. The ED will be a fragment of an enzyme that can be complemented with another fragment, the EA, to form an active enzyme. The ED fragment of the fusion protein will complex with the EA fragment owing to the affinity of the fragments for each other.

In other embodiments, the complementing fragments are high affinity fragments. High affinity components are generally two fragments of an enzyme with the fragments having sufficiently high affinity such that they can spontaneously bind to each other and reform a fully functional enzyme or enzyme subunit. Typically, at least 5% of enzymatic activity of the native enzyme is achieved when mixed under appropriate conditions in solution, sometimes about 10, 20, 30, 40, 50, 60, 70, 80, 90, 95, 99, or 100% of the enzymatic activity of the native enzyme. Determination of such activity can be performed using routine methods with the concentration at which the complemented enzyme and parental enzyme are compared typically being the same with a range of, e.g., between $10^{-3}$ to $10^{-6}$M. High affinity components permit monitoring of the presence, absence, or increase of the complementing fragments as they form a complex with the interacting partner. For example, if one complementing fragment is present in the fusion protein (fused to the target macromolecule) and forms a complex with the test compound then the incubation with the second fragment after lysis of the cell will result in detectable enzymatic activity, thus permitting the analysis of cellular interactions. Accordingly, if the amount of high affinity components increases in the assay system, then the amount of detectable enzymatic activity will increase proportionally. Typically, large increases in the amount of activity are detectable up to a 1:1 reporter component ratio. See e.g., the experimental section below, as well as U.S. patent application Ser. No. 11/132,764 filed on May 18, 2005 for a review of such a rational approach as employed with an initial high affinity β-galactosidase complementation reporter system.

In a specific embodiment, the α peptide employed is one that complements the ω peptide robustly in mammalian cells. The high affinity minimal a peptide permits sensitive, accurate analysis of cellular interaction events between various intracellular entities with only a minimum of interactions required for detection. Exemplary high affinity α peptides (enzyme donors) include

```
(Wild-type ED) SEQ ID NO. 1:
MGVITDSLAVVLQRRDWENPGVTQLNRLAAHPPFASWRNSEEARTDRP

SQQL (Prolabel, or "PL" ED) SEQ ID NO. 2:
NSLAVVLQRRDWENPGVTQLNRLAAHPPFASWRNSEEARTDR, (modified ED, W34Y ), SEQ ID NO. 3:
MGVITDSLAVVLQRRDWENPGVTQLNRLAAHPPFASYRNSEEARTDRP

SQQL.
```

Another applicable ED is termed enhanced prolabel, SEQ ID NO. 4 below

```
NSLAVVLQRRDWENPGVTQLNRLAAHPPFASWRNSEEARTDR
```

A range of methods are available to measure the enzyme activity of β-galactosidase which include live cell flow cytometry and histochemical staining with the chromogenic substrate 5-bromo-4-chloro-3-indolyl β-D-galactopyranoside (X-Gal). See e.g., Nolan et al., Proc. Natl. Acad. Sci., USA, 85: 2603-2607 (1988); and Lojda, Z., Enzyme Histochemistry: A laboratory Manual, Springer, Berlin, (1979). Vital substrates for β-gal, which can be used in living cells, are also encompassed by the presently disclosed methods and materials. For example, a fluorogenic substrate, resorufin β-galactosidase bis-aminopropyl polyethylene glycol 1900 (RGPEG) has been described. Minden (1996) Bio-Techniques 20(1): 122-129. This compound can be delivered to cells by microinjection, electroporation or a variety of bulk-loading techniques. Once inside a cell, the substrate is unable to escape through the plasma membrane or by gap junctions. Another vital substrate that can be used in the practice of the presently disclosed methods and materials is fluorescein di-β-D-galactopyranoside (FDG), which is especially well-suited for analyses for analysis by fluorescence-activated cell sorting (FACS) and flow cytometry. Nolan et al., Proc. Natl. Acad. Sci, USA, 85:2603-2607 (1988) and Rotman et al. (1963) Proc. Natl. Acad. Sci, USA 50:1-6.

The active reconstituted β-galactosidase may also be detected using a chemiluminescence assay. For example, cells containing β-galactosidase fusions are lysed (with or without contacting with a crosslinking agent) in a mixture of buffers containing Galacton Plus substrate from a Galactolight Plus assay kit (Tropix, Bedford Mass.). Bronstein et al, J. Biolumin. Chemilumin., 4:99-111 (1989). After addition of Light Emission Accelerator solution, luminescence is measured in a luminometer or a scintillation counter.

Fusion Protein

As disclosed in the present application, a macromolecule of interest is fused to a labeling peptide to form a fusion protein. A fusion protein includes a single continuous linear polymer of amino acids which includes the full or partial sequences of two or more macromolecules or two or more distinct proteins. Methods for the construction of fusion proteins are known in the art. A fusion protein gene construct may also include a single continuous linear polymer of nucleotides which encodes the full or partial sequences of two or more distinct proteins in the same uninterrupted reading frame. Further, the fusion gene construct of the invention is introduced into the cells to assay for ligand binding following denaturation. The fusion gene construct may be introduced into cells by any method of nucleic acid transfer known in the art. Different fusion gene constructs encoding unique fusion proteins may be present on separate nucleic acid molecules or on the same nucleic acid molecule.

The fusion protein may also comprise a target macromolecule fused to a β-gal fragment as a labeling peptide. Thus, in some embodiments, the fusion protein as used in the present assay comprises a protein of interest and a labeling peptide, which, after treatment, is contacted with a second label (enzyme fragment, antibody, etc.) to generate a signal.

Use of a Protein as a Target Macromolecule (Target Protein)

The protein used as a target macromolecule can be any conceivable polypeptide or protein that may be of interest, such as to study or otherwise characterize. Proteins of interest may include transferase, oxidoreductase, hydrolase, ligase, and isomerase, along with kinases, phosphatases, carboxylases, phosphodiesterases, dehydrogenases, oxidases, peroxidases, proteases, signaling proteins, metalloproteins, cytoplasmic proteins and nuclear localization proteins. The target protein may be obtained from any source such as a natural occurring source, e.g., cells, tissues, biological fluids, tissue biopsies, soil, water, etc.

The bromodomain protein family is the family described in the SCOP database, http(colon slash slash) scop.mrc-lmb.cam.ac.uk/scop-1.75/data/scop.b.b.ec.b.b.html. Of particular interest is the BET family of bromodomain proteins, e.g. BRD1-BRD4 and related proteins, as described at Filippakopoulos et al., "Selective inhibition of BET bromodomains," Nature 468: 1067-1073 (23 Dec. 2010).

Target proteins may also include cell membrane proteins, defined as proteins that interact with biological membranes and comprise integral membrane proteins and peripheral membrane proteins. Target proteins may also include signaling proteins that govern basic cellular activities and coordinate cell actions.

Kits

Also provided by the subject invention are kits for use in practicing one or more of the above described applications. In certain embodiments, kits at least include a cell that expresses, either constitutively or inducibly, a fusion protein that includes a DNA binding domain, a protein of interest and a β-galactosidase fragment, as reviewed above. In certain embodiments, kits include elements for making such cells, e.g., nucleic acids encoding a fusion protein present on vectors and/or nucleic acids encoding a β-galactosidase fragment to which proteins of interest can be fused using standard molecular biology techniques, as reviewed above.

The kits may further include one or more additional components which find use in practicing certain embodiments of the invention, including but not limited to enzyme substrates, cell growth media, etc.

In certain embodiments, the kit may include (a) a cell comprising: a fusion protein comprising a DNA binding domain, a protein of interest and an ED fragment of β-galactosidase, (b) an EA fragment of β-galactosidase and (c) a β-galactosidase substrate.

In certain embodiments, the kit may include (a) a cell comprising: a fusion protein comprising the target and an ED fragment of β-galactosidase; (b) an EA fragment of β-galactosidase; and (c) a β-galactosidase substrate.

Also provided are kits that include (a) a cell comprising: a fusion protein comprising the DNA binding domain, a protein of interest and an ED fragment of β-galactosidase; (b) a test compound, (c) an EA fragment of β-galactosidase; and (d) a β-galactosidase substrate.

Also provided are kits that include (a) a cell comprising: a fusion protein comprising the DNA binding domain, a protein of interest and an ED fragment of β-galactosidase; (b) a small molecule, (c) an EA fragment of β-galactosidase; and (d) a β-galactosidase substrate.

Also provided herein are kits that comprise an expression construct encoding a fusion protein comprising a target peptide fused to an ED fragment of β-galactosidase.

In certain embodiments, the vector comprises a restriction site positioned on a vector such that when a protein coding sequence is inserted into the vector using the restriction site, the vector encodes a fusion protein of the target and the β-galactosidase fragment. In certain embodiments, the kit further comprises a mammalian cell.

In addition to the above components, the subject kits may further include instructions for practicing the subject methods. These instructions may be present in the subject kit in a variety of forms, one or more of which may be present in the kit. One form in which these instructions may be present is as printed information on a suitable medium or substrate, e.g., a piece or pieces of paper on which the information is printed, in the packaging of the kit, in a package insert etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

Figure 3:
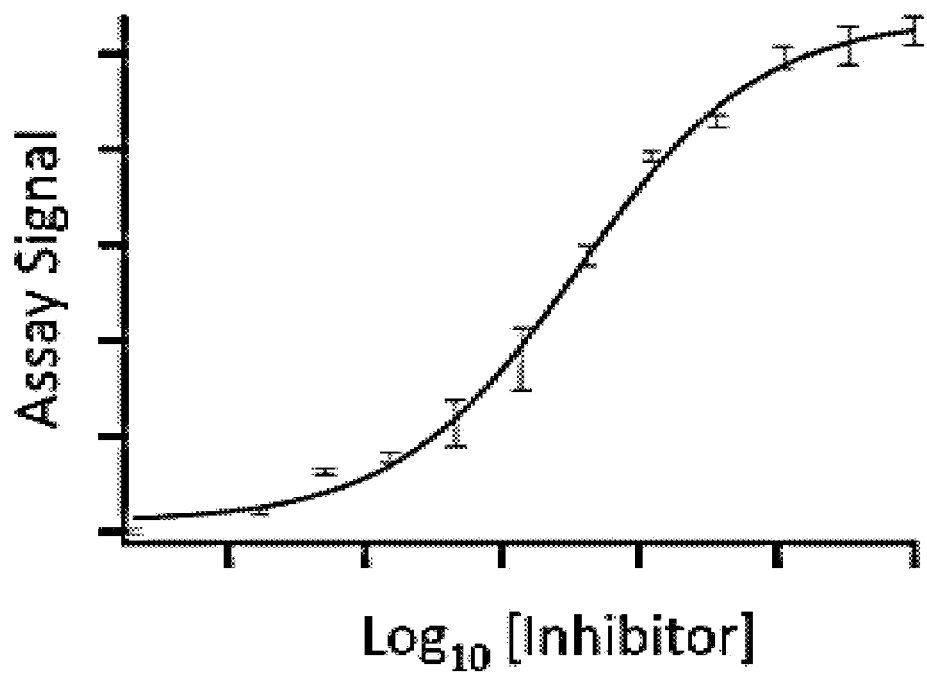
FIG. 3 shows a graph of a fusion protein of BRD4(1)-Prolabel™ ED in a crude cell extract incubated with an indicator and heated at about 45° C. for 30 seconds. An inhibitor that binds to the BRD4 (1) is added at different concentrations between 0 and 100 uM. It can be seen that a dose-response protection of the fusion/BRD4(1) is achieved by binding of the inhibitor. In all of the Figures illustrating BRD4(1), the construct used is NFκB DNA Binding Domain-Linker-BRD4(1)-Linker-ED. The NFκB DNA binding domain sequence in the fusion protein does not play an active role in these examples.
Figure 4:
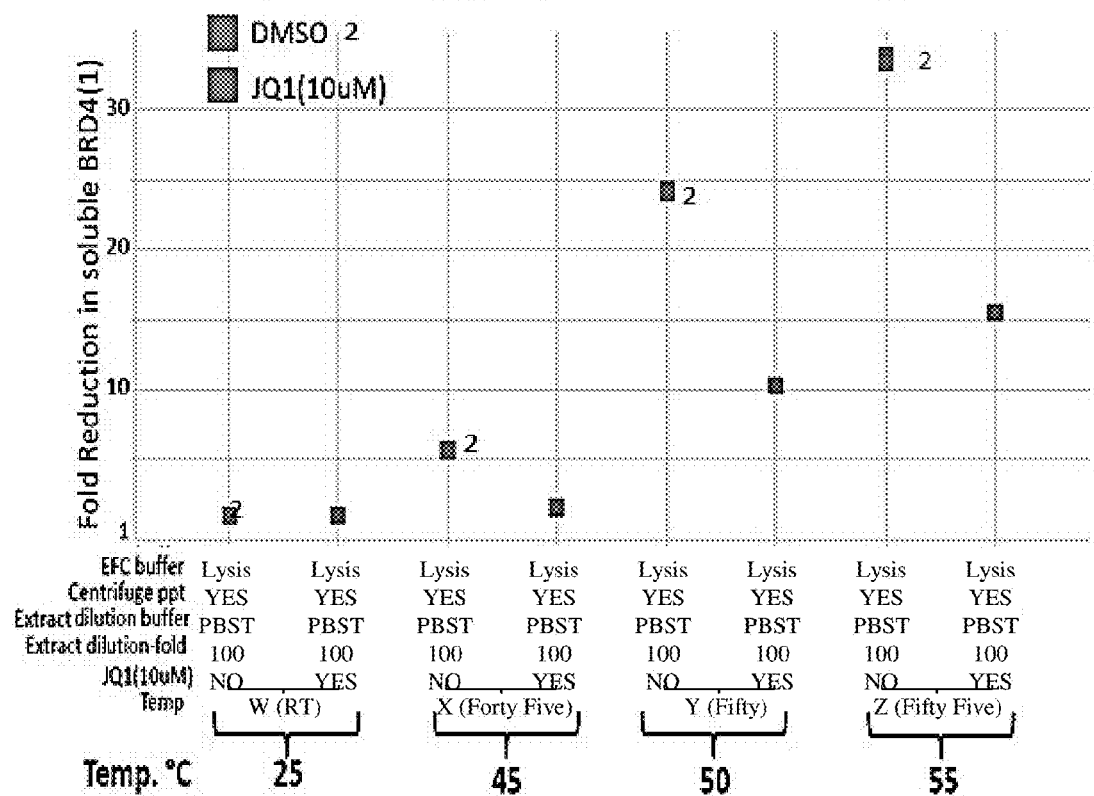
FIG. 4 is a plot comparing a non-inhibitor DMSO (labeled "2") with JQ1, (6S)-4-(4-Chlorophenyl)-2,3,9-trimethyl-6H-thieno[3,2-f][1,2,4]triazolo[4,3-a][1,4]diazepine-6-acetic acid, 1,1-dimethylethyl ester, known to be a selective BET bromodomain inhibitor. As can be seen, the solubility of the BRD4(1) is reduced by a significant amount at temperatures between 45 and 55° C., while the presence of JQ1 at 10 uM caused the reduction of solubility to be much less.
Figure 5:
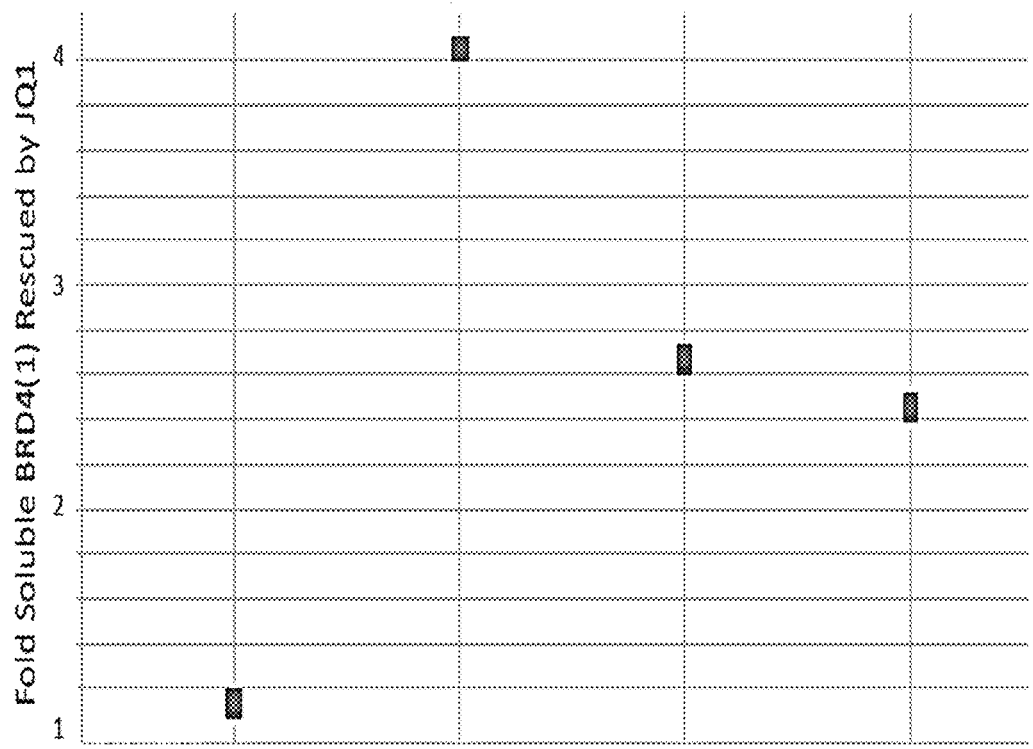
FIG. 5 is a plot that also shows protection of BRD4(1) at 45, 50 and 55° C. in the presence or absence of JQ1 binding to the BRD4(1). As shown at the arrow, the protection from heat denaturation (insolubility) at 45° C. is more significant than at 25, 50, or 55° C. The incubation at 25° C. was run as a control, not to indicate thermal denaturation.

The present working examples demonstrate that the thermal denaturation of a BRD4(1)-ED fusion can be measured in a facile, sensitive, and precise manner by using enzyme fragment complementation (EFC) (FIGS. 4 and 5). Furthermore, the observed denaturation can be rescued by the presence of small molecule BRD4(1) inhibitors in a dose-dependent manner (FIGS. 3-7). The method is homogeneous and does not require wash steps or centrifugation (FIG. 6) and is thus amenable to high throughput applications; and the resultant data have high precision (FIGS. 3 and 7). The method can be used to distinguish molecules with different potencies for BRD4(1) as well (FIG. 7).

Example 1

Measuring Binding of BRD4(1) ED Fusion Protein with a Known Ligand (JQ1)

The present experiment was done to study binding of a ligand to BRD4(1) fusion protein under heat stress and if the ligand binding protects the fusion protein from denaturation.

To carry out the assay, a fusion protein [BRD4(1)-ED], which also contains an NFκB DNA binding domain at the N-terminus, was constructed with BRD4(1) and a Prolabel™ ED fragment. The fusion protein in crude cell extract was incubated with a known potent inhibitor (JQ1) in a concentration ranging from 0-100 3M. The incubation was for 1 hour at room temperature. The samples were then heated to 45° C. for 30 s. EA was subsequently added into the samples (along with luminescent substrate for beta-galactosidase) and complementation was measured by measuring luminescence. As shown in FIG. 3, binding of the inhibitor to BRD4(1) fusion protein and binding could rescue the fusion protein from denaturation in a dose-dependent manner. Exquisite precision was obtained for duplicate samples.

Example 2

Measuring Thermal Denaturation of BRD4(1) in the Presence and Absence of JQ1

The present experiment was done to study denaturation/precipitation of BRD4(1) in the presence and absence of an inhibitor. The inhibitor as used in the present experiment is JQ1.

To carry out the assays, two separate samples were prepared wherein one sample comprises BRD4(1)(fusion) and no inhibitor whereas another sample comprises BRD4 (1)(fusion) and an inhibitor. The inhibitor as used in the present experiment is JQ1 and was used at a concentration of 10 3M. Following incubation, samples were exposed to increased temperatures (25° C., 45° C., 50° C. and 55° C. respectively). The samples were then centrifuged to separate the precipitate. As can be seen from FIG. 4, JQ1 bound to the fusion protects BRD4(1) from precipitation as compared to BRD4(1) with no inhibitor binding.

Example 3

Measuring Precipitation of BRD4(1) Fusion Protein in the Presence of JQ1

The present experiment was done to study how binding of JQ1 protects BRD4(1) fusion protein from temperature induced precipitation.

To carry out the experiment, a fusion protein was constructed comprising NFκB-BRD4(1)-ED. The fusion protein from cell lysate was incubated with JQ1 (10 μM). The samples were then exposed to several temperatures (25° C., 45° C., 50° C. and 55° C. respectively). As can be seen from FIG. 5, fold soluble BRD4(1) was maximally rescued at 45° C., and proteins slowly started precipitating at higher temperatures.

Example 4

The Effect of Centrifugation on the Assay Readout

The present experiment was done to study the importance of centrifugation to separate precipitated fusion protein in a composition also containing soluble, bound fusion protein, and how it affects the final readout.

To carry out the experiment, a fusion protein was constructed comprising NFκB-BRD4(1)-Prolabel (ED). The fusion protein was then incubated with a ligand and lysis was done using FLASH lysis and in PBS. The samples were then kept at room temperature or exposed to 45° C. elevated temperature. Each sample was divided into 2 wherein one part was centrifuged and other part of the sample was not centrifuged.

Figure 6:
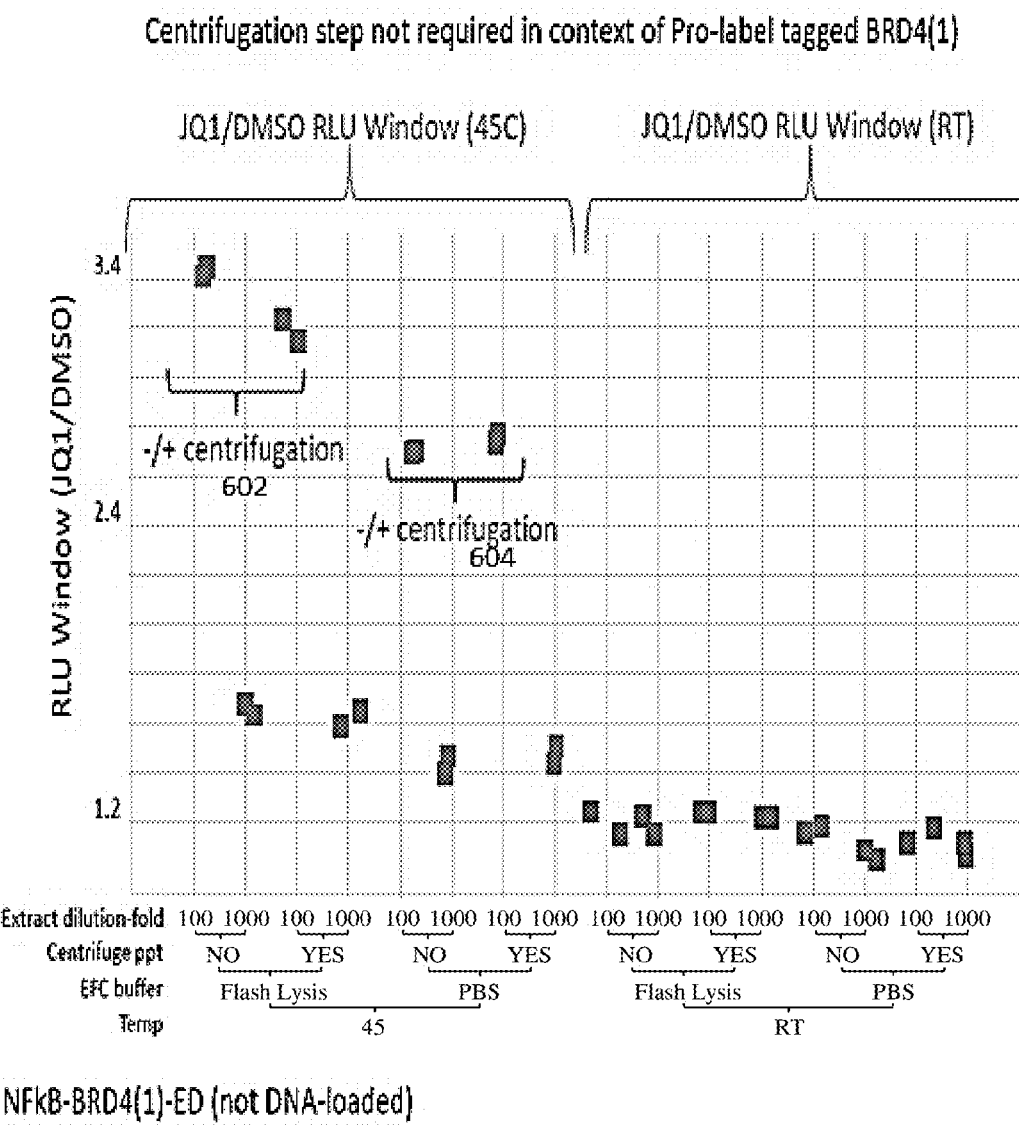
FIG. 6 is a plot of the RLU (relative luminescence units) showing that little difference is seen whether or not centrifugation is carried out, as shown by the closely spaced spots at 602 and 604.
Figure 7:
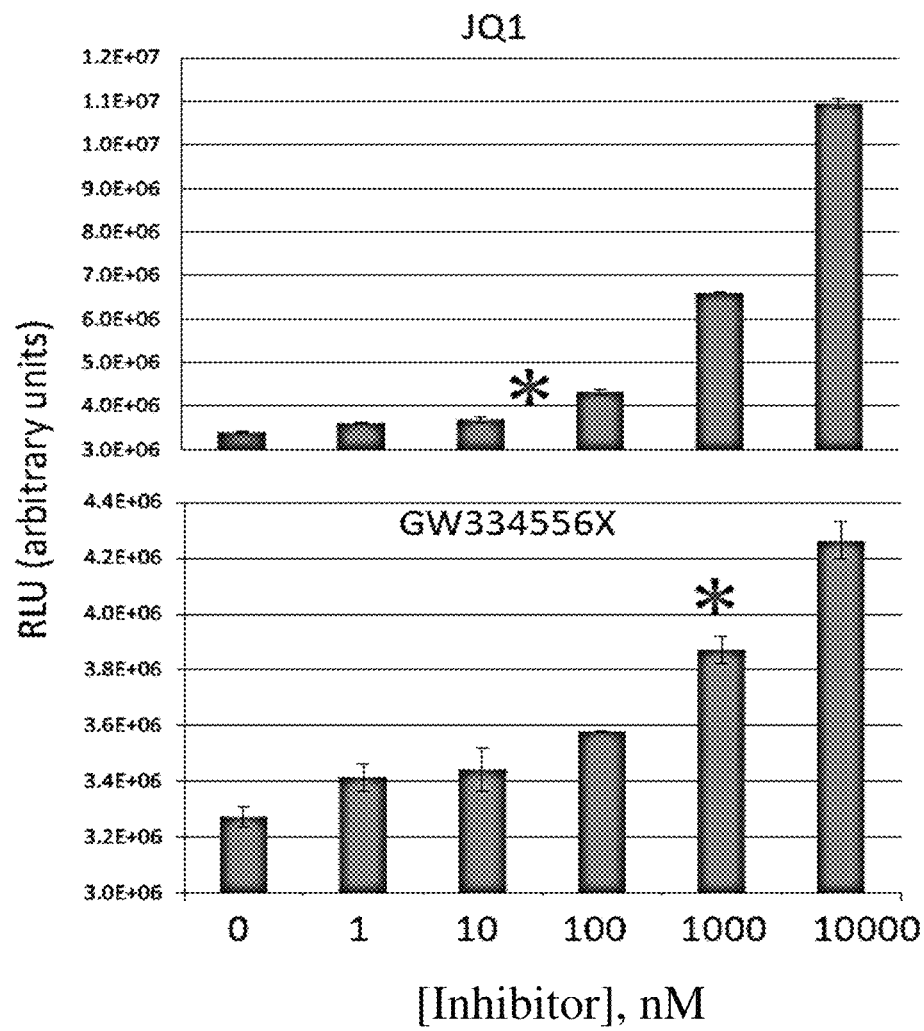
FIG. 7 is a pair of bar graphs showing dose response relationships in the ligand binding assay with potent BRD4 (1) inhibitor JQ1 (top figure) and a known, less potent BRD4(1) inhibitor GW334556X (bottom figure). BRD4(1)-Prolabel™ ED fusion protein in a crude cell extract was incubated with an indicator and heated to a target temperature in a PCR thermal cycler machine. The asterisks indicate the $K_D$ (dissociate constant) concentration as measured by the BROMOscan® Technology Platform available from DiscoveRx Corp. This shows that the present assay can accurately determine binding constants. The coefficient of variance observed here was less than 1%. The assay is also very reproducible. GW334556X is further described in Chung et al. J. Med. Chem. (2012) 55: 576.

As can be seen from FIG. 6, there is little difference in the assay readout whether the sample was centrifuged to separate the precipitate or not. Therefore, the experiment shows that centrifugation is not required in the present assay and the ligand binding can be assayed using EFC in the crude cell extract.

Example 5

Dose-Response Curves for Known BRD4(1) Inhibitors Following Ligand Binding Assay The present experiment was done to determine the dose-dependence of ligand protein binding following the ligand binding assay as described in the present application.

To carry out the assay, a fusion protein was constructed as described above. The fusion protein was then incubated with a ligand (JQ1 and GW334556X) respectively, as shown in FIG. 7. The incubation at the indicated concentrations was at room temperature for 1 hour with 1:100 diluted extract (about 10 nM BRD4(1) concentration). The samples were then heated to 45° C. for 3 minutes followed by adding EA and a luminescent beta-galactosidase substrate (Flash Substrate) to measure complementation. The error bars indicate 3× standard deviation (99.7% confidence interval). Interactions were detected with high statistical significance when compounds were screened at ≥3× the $K_D$ concentration.

Inhibitor $K_D$ values measured by another method (BROMOscan® are indicated by * (align * to x-axis concentration value). BROMOscan® has been developed by DiscoveRx Corporation, Fremont, Calif. The BROMOscan® platform measures the interactions between test compounds and a panel of bromodomain assays. See more at: http(colon/slash/w-w-w.discoverx.com/technologies-platforms/competitive-binding-technology/bromoscan-technology-platform#sthash.Zj axX6mR.dpuf).

Example 6

Comparison Between a Standard Denaturation Protocol and a Pulse Denaturation Protocol The methods of Examples 1-5 can be implemented by a number of heating steps. The following examples pertain to a protocol in which the macromolecules (e.g. proteins) are heated at a temperature that does not, in a single heating step, cause significant denaturation (melting) but that, in a series of heating steps, does. The steps are applied such that one heating step, which is not effective to melt the protein, is followed by a series of heating steps that, cumulatively, do cause denaturation (in the absence of a ligand). For accomplishing this, a thermoelectric heating and cooling device may be employed and preprogrammed to carry out pre-defined heating and cooling (non-heating) steps. The preferred thermoelectric heating and cooling device is based on a Peltier Junction. These devices can carry out active heating and cooling; alternatively, the present devices may be provided with a large heat sink. Details of Peltier heating and cooling of substrates and masks may be found at U.S. Pat. No. 3,161,542. The methods described below may comprise a number of heating steps, separated by cooling steps, and a series of one or more heating temperatures. These numbers can be determined using the teachings herein. The method may be carried out with a heating step based on the properties of the macromolecule that is the binding target. Once a temperature T and a time t are determined, T may be reduced in increments, preferably below the melting temperature of the macromolecule, and the time t can be subdivided into a series of heating steps whose total, at least initially, is total time. Cooling steps may be based on the equipment used to return the reaction mixture to ambient or near ambient temperature (~25° C.). Possible, non-limiting, combinations are 10-70 pulses at 37-50° C. for 5-10 seconds, with a 15 second to 2 minute cooling interval. Other examples are given below. The volume of the reaction mixture should also be considered, where larger volumes suggest the use of more and longer pulses.

As shown in FIG. 8A, a standard denaturation profile comprises a single cycle of a high temperature pulse followed by an extended denaturation time for protein denaturation. A pulse denaturation profile, in contrast, comprises several cycles of a heat pulse at a mild temperature which is followed by a brief denaturation and a resetting to a lower temperature (FIG. 8B). The temperatures in FIGS. 8A and 8B represent heat settings. The temperature in the mixture will, as is known follow a curve. The cooling steps in FIG. 8B will result in a ramp up of the mixture over time, according to the embodiment. That is, the existing temperature of the mixture during a cooling step remains greater than a temperature in the mixture that may be existent and measured during in a previous cooling step.

The temperature for a standard denaturation protocol may be 45° C. or higher whereas the temperature for a pulsed denaturation is 40° C. or lower than 40° C. Denaturation of macromolecules runs in minutes in a standard denaturation protocol whereas in a pulse denaturation protocol there is a brief denaturation step running in seconds followed by reduction of the temperature to room temperature or even lower before the next heat pulse.

Example 7

Mathematical Modeling Studies

Figure 9:
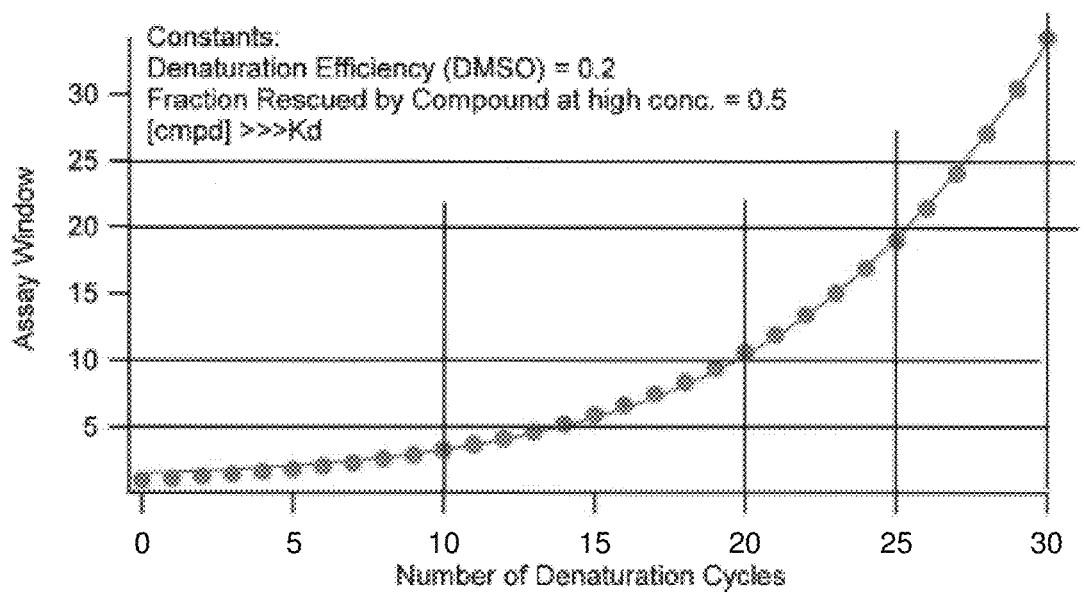
FIG. 9 is a graph showing a mathematical model calculating an assay window versus the number of denaturation cycles. It shows that the assay window grows exponentially with cycle number. "Assay window" is defined as luminescence signal in the presence of known ligand divided by luminescence signal in the absence of known ligand after x cycles. The model assumes that a low fraction of folded protein denatures each cycle and cannot refold/reactivate on subsequent cycles. The model assumes that, in each cycle, the known ligand rescues 50% of the protein from denaturation. The model also assumes that compound binding returns to room temperature levels each cycle during temperature shift from set point to room temp. The degree to which compound binding protects the protein from denaturation and the total amount of denaturation for the no compound control denaturation/naturation in dictate the assay window. An assay window may be estimated from data presented here by comparing the base line signal (RLU) to the maximum signal in a given experiment.

FIG. 9 shows results of a mathematical modeling showing advantages of pulse denaturation. The Y axis on the graph shows an assay window which is defined as luminescence signal in the presence of known ligand divided by luminescence signal in the absence of known ligand after X no. of cycle. The X axis on the graph shows the number of denaturation cycles wherein the denaturation is done by pulse heating.

The model is based on an assumption that a low fraction of folded protein denatures during each cycle and cannot refold or reactivate on subsequent cycles, while incubating the protein with a known ligand rescues half or more than half of the protein from denaturation. The protein ligand binding level returns to room temperature or below level during each cycle when the temperature is brought down to room temperature or lower.

The mathematical modeling graph shows that multiple cycles of gentle denaturation provides better ligand binding assay results without compromising on assay sensitivity, which is the same when compared to the standard denaturation protocol.

Example 8

Figure 10:
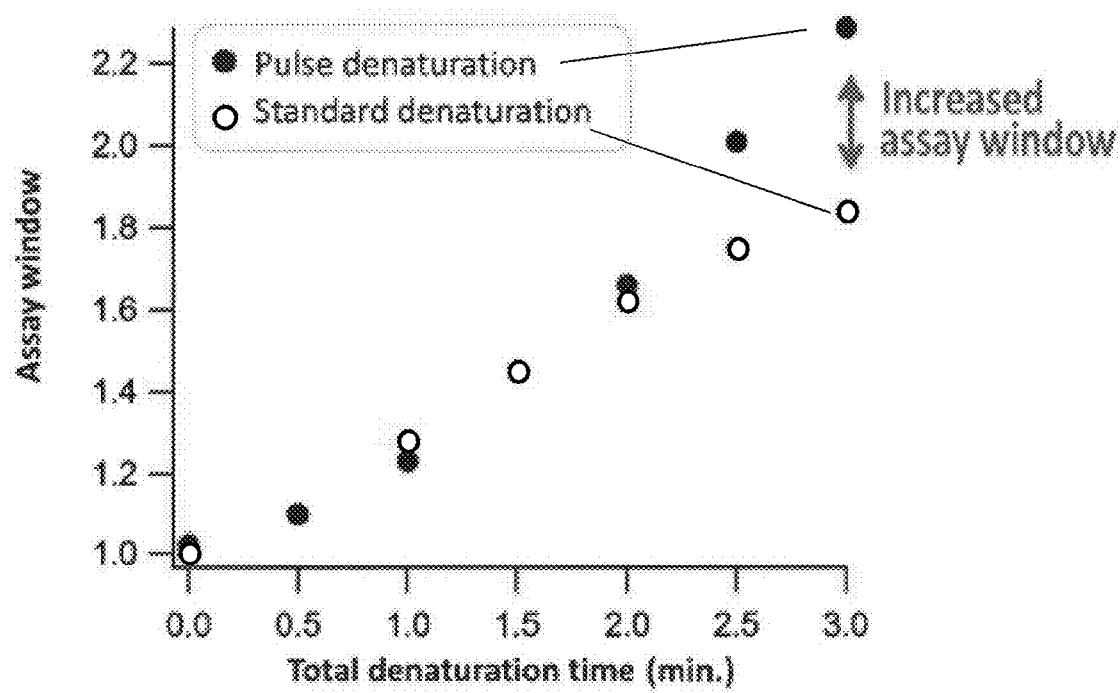
FIG. 10 is a graph comparing a "standard" (constant heat) protocol with a pulse protocol. The assay window for the pulse denaturation is shown in black circles. The pulse system results, over time, in an increased assay window in comparison to the standard denaturation, which is shown in white circles. Thermal melting assay windows for both "standard" and "pulse" protocols were measured for the BRD9-Bromosporine interaction. Bromosporine is N-[(6-3-Methanesulfonamido-4-methylphenyl)-3-methyl-[1,2,4]triazolo[4,3-b]pyridazin-8-yl]carbamate, commercially available from Tocris Biosciences.

Study of BRD9-Bromosporine Binding Using Standard and Pulsed Denaturation Protocols FIG. 10 shows a dose response curve for BRD9-bromosporine binding following standard and pulsed denaturation protocols. Cell extracts containing the ED tagged BRD9 were diluted in PBST and incubated for 1 hour at room temp. with 25 uM Bromosporine or with 0.1% DMSO/0.9% MEG (49.5 ul cell extract+0.5 ul 2.5 mM Bromosporine or 0.5 ul 10% DMSO/90% MEG). The samples were then subjected to heat denaturation at 45° C. either with the pulse method or with the standard (one step) denaturation protocol. In the first case the samples were repeatedly exposed to 45° C. for 0.5 min (with a 1 minute interval at room temperature between heat pulses) to a total heating time between 0.5 to 3 minutes ("Pulse denaturation", dark circles). In the second case the samples were heated up for the same total amounts of time (0.5 min to 3 minutes) but in a single step ("standard denaturation", white circles).

Soluble protein was then quantified by EFC (heat denaturation renders the ED inaccessible for complementation to EA). EFC reactions were set up as follows: 5 ul cell extract was incubated for 30 min with 10 ul EA, 10 ul EA Dilution Buffer, 20 ul Flash lysis buffer, 20 ul Flash Substrate, and 135 ul PBS. Assay windows were calculated by dividing the RLU signal of the protein with bromosporine by the RLU of the protein with DMSO/MEG.

As can be seen from the curve, the assay window improved with pulse denaturation (6 repetitive pulses, with a total of 3 minutes of heating) giving improved binding assay results without extend heating.

Example 9

Study of CREBBP/SGC-CBP-30 Binding Using Standard and Pulsed Denaturation Protocols FIG. 11 shows a dose response curve for CREBBP/SGC-CBP-30 binding following standard and pulsed denaturation protocols. (CREBBP is CREB binding protein having the official symbol CREBBP; SGC-CBP-30 is small molecule that is selective inhibitor of CREBBP, having IUPAC name (S)-4-(1-(2-(3-chloro-4-methoxyphenethyl)-5-(3,5-dimethylisoxazol-4-yl)-1H-benzo[d]imidazol-1-yl)propan-2-yl) morpholine. Cell extracts containing ED tagged CREBBP were incubated for 1 hour at room temperature with serial dilutions of SGC-CBP30 (49.5 ul cell extract diluted in PBST+0.5 ul of 100× compound in 10% DMSO/90% MEG) and then heat denatured in the conditions indicated on the graph. Soluble protein was quantified by EFC with the same protocol used for BRD9. Data were fitted with the Hill Equation and EC50s were calculated. FIG. 11 shows that the pulse denaturation shows a higher signal at a lower concentration of inhibitor and still shows a dose response curve over the entire range between minimum and maximum detectible concentrations.

Example 10

Study of ABL1 Binding to a Range of Small Molecule Inhibitors Using Pulsed Denaturation FIG. 12 shows pulse denaturation technology applied to a protein kinase (ABL1) to test a range of small molecule inhibitors known from the literature to bind this target with a wide range of affinities. $EC_{50}$ dose response curves for the seven inhibitors shown on the graph (inhibitor name labels and corresponding curves are in the same left to right order) were measured against ED-tagged ABL1. The overall procedure used was similar to that described for Example 9 and used a pulse denaturation sequence of 30 cycles of: 7 seconds at 42° C. followed by 60 seconds at 25° C. The affinity of the inhibitors for ABL1 decreases from left to right on the graph; the leftmost curve identifies the inhibitor of highest affinity and the rightmost curve identifies the one of lowest affinity. Ordered from higher to lower affinity, the inhibitors are dasatinib, ponatinib, imatinib, VX-680, staurosporine, SU-14813, and purvalanol B. The potency rank order for these seven inhibitors is in good agreement with published values (Davis et al. Nat Biotechnol. 2011 Oct. 30; 29(11):1046-51. doi: 10.1038/nbt.1990.).

At each concentration, the inhibitors can be compared as to their degree of binding to ABL1. At an inhibitor concentration of 1 nM, for example, a maximal signal is seen for dasatinib but a minimal signal is seen for staurosporine. This means that at this concentration, dasatinib protects ABL1 against denaturation to a much greater degree than staurosporine does, a result that reflects the higher affinity of dasatinib for ABL1.

Example 11

Study of Methyl Transferase G9a/UNC-0638 Binding Using a Standard Denaturation Protocol FIG. 13 shows denaturation protocol applied to a protein methyltransferase (G9a) to test the known inhibitor UNC-0638 in a dose response curve. UNC-0638 was tested against ED-tagged G9a, and the overall procedure used was similar to that described for Example 9. This proof of concept G9a study was performed using a single denaturation step of 3 minutes at 50° C. The increase in the assay signal starting at about $10^2$ nM and continuing through $10^4$ nM shows that the protection against denaturation of G9a increases in a dose-dependent manner with the concentration of the inhibitor. The protection results from inhibitor binding, the associated $EC_{50}$ value of which may be derived from the curve. This example, along with the other examples disclosed herein, shows that the assay may be used to measure binding of compounds to a wide variety of macromolecules.

This example shows that a single heat pulse at 50° C. for 3 minutes yield a useful assay with a methyltransferase enzyme and indicates the broad applicability One may refer to the comparison between the present "standard," or single pulse, compared with a multi-pulse protocol and expect that the present assay window would be improved by a pulse protocol.

Example 12

Kit for Measuring Inhibitors of BRD4(1)

The exemplary kit is prepared as a 96-well plate format kit for the in vitro biochemical assessment of BRD4(1) inhibitor potency. The assay uses enzyme fragment complementation (EFC) and pulse denaturation technologies to measure ligand-dependent thermal stabilization of target proteins. This approach enables the measurement of quantitative inhibitor EC50 values. The kit provides sufficient reagents to perform four 96-well plate experiments (16×12 point dose-response curves in duplicate) and is optimized for the measurement of inhibitor EC50 values. The streamlined and rapid assay protocol does not require cumbersome sample processing, plate transfer, or centrifugation steps. The assay provided in this kit is not optimized for single concentration screens of compound collections. The kit may be used to validate screening hits identified by related or orthogonal methods; monitor compound potency improvements during lead optimization; obtain rapid results (less than 4 hours start to finish), with less than 60 minutes of hands-on time; and measure inhibitor EC50 values over a broad potency range (high picomolar to millimolar). The kit includes a fusion of the protein of interest with a beta galactosidase enzyme fragment ("PL"); a positive control, dilution buffer and two enzyme substrate reagents-β galactosidase fragment complementing PL; and β galactoside substrate.

Step 1 of the exemplary kit instructions is to prepare the test and control compounds in serial dilutions. One prepares a series of dilutions. Then the BRD4-PL reagent is added and the mixture is incubated. Step 2 is to set up compound binding reaction set up. Step 3 is instructions for a pulse denaturation protocol. The pulse denaturation protocol is summarized as follows: a. Transfer PCR plate to a thermocycler and perform 40 pulse denaturation cycles. One denaturation cycle is defined as: 7 seconds at 40° C. followed by 60 seconds at 25° C. b. After the cycling program is complete, the plate can be read-out by EFC immediately or stored at −80° C. if the readout is to be performed at a later time. The thermocycler's heated lid is ideally set to 40° C., but some instruments have a default setting of ≥95° C., which is also acceptable. Step 4 of the instructions describe the EFC detection protocol in each well of the assay plate. Step 5 comprises instructions for reading the samples on a luminescence plate reader at 1 second/well and data analysis which will show a dose response of the compound(s) tested.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, for the purpose of describing and enabling the method or material referred to.

What is claimed is:

1. A method for measuring a binding property between a compound and a target macromolecule, comprising:
    (a) preparing a fluid mixture comprising (i) a chimeric molecule comprising a target macromolecule subject to denaturation linked to a labeling peptide and (ii) a compound being measured for binding to the target macromolecule;
    (b) incubating the fluid mixture of step (a) under conditions permitting binding of said compound to target macromolecules in the mixture;
    (c) treating the fluid mixture of step (b) under conditions that cause a differential denaturation between chimeric molecules bound to the compound and chimeric molecules not bound to the compound; and
    (d) generating a signal from chimeric molecules subjected to said differential denaturation in step (c), by adding to the mixture a second label that reacts with the labeling peptide in the chimeric molecule, wherein,
    (e) the signal in step (d) is detected and indicates a binding property between the compound and the target macromolecule.

2. The method of claim 1, wherein said differential denaturation comprises heating the fluid mixture in a step that is that one of (a) multiple heating steps and at least one cooling step between heating steps and (b) a single heating step.

3. The method of claim 2, wherein the target macromolecule is a protein.

4. The method of claim 3, wherein the labeling peptide is an epitope tag.

5. The method of claim 3, wherein the labeling peptide is between 10 and 100 amino acids in length.

6. The method of claim 5, wherein the labeling peptide is an enzyme fragment and the second label is a complementary enzyme fragment which combines with the labeling peptide to create an active enzyme.

7. The method of claim 6, wherein the labeling peptide is an enzyme donor ("ED") active in enzyme fragment complementation of β-galactosidase and being fused to a terminus of a protein that is the target macromolecule.

8. The method of claim 7, wherein the ED is one of SEQ ID NO: 1, SEQ ID NO: 2, SEQ ID NO: 3, or SEQ ID NO: 4.

9. The method of claim 5, wherein the compound is a small molecule.

10. The method of claim 9, wherein the small molecule is one that binds to an active site on the target macromolecule.

11. The method of claim 5, wherein said differential denaturation is a step of heating the mixture to a temperature that is one of between 30° C. and 50° C.

12. The method of claim 11, wherein said heating comprises multiple heating steps for a defined period of time between 0.1 and 5 minutes.

13. The method of claim 12, wherein said heating step comprises applying heat to the mixture between 40° C. and 45° C., and further comprises multiple steps of heating for a time of 0.1 to 5 minutes.

14. The method of claim 13, wherein multiple steps of heating steps comprises an individual cooling step between individual heating steps, of being between 10 seconds and 2 minutes in duration.

15. The method of claim 14, comprising between three and ten cooling steps.

16. The method of claim 15, wherein said a temperature of the mixture during a cooling step remains greater than a temperature in a previous cooling step.

17. The method of claim 14, wherein said cooling steps comprise actively cooling the mixture.

18. The method claim 1, wherein the step of denaturation comprises the addition of a strong acid or base, a concentrated inorganic salt, an organic solvent, or exposure to radiation.

19. The method of claim 18, wherein the organic solvent is alcohol or chloroform.

20. A method for measuring a binding property between a compound and a target macromolecule that is a protein, comprising:
    (a) preparing a fluid mixture comprising (i) a chimeric molecule comprising a protein target macromolecule that is subject to denaturation linked to a labeling peptide and (ii) a compound being measured for binding to the target macromolecule;
    (b) incubating the fluid mixture of step (a) under heating conditions permitting binding of said compound to target macromolecules in the mixture;
    (c) treating the fluid mixture of step (b) under conditions that cause a differential denaturation between chimeric molecules bound to the compound and chimeric molecules not bound to the compound;
    (d) generating a signal from chimeric molecules subjected to said differential denaturation using enzyme fragment complementation between the labeling peptide and a complementary enzyme fragment;
    (e) repeating steps (a) through (d) with mixtures containing different dilutions of the compound, wherein
    the signals in step (e) is detected and indicate a binding property between the compound and the target macromolecule, comprising a dose-response curve of the compound.

21. The method of claim 20 wherein repeated steps (a) through (e) are used to calculate a binding constant ($K_D$) of binding of compound to the target macromolecule.

22. The method of claim 20, wherein the target macromolecule is a protein which is one of a bromodomain protein, a protein kinase or a histone methyltransferase.

* * * * *